(12) United States Patent
Pandey et al.

(10) Patent No.: US 8,361,462 B2
(45) Date of Patent: Jan. 29, 2013

(54) ANTI-APOPTOTIC PROTEIN ANTIBODIES

(75) Inventors: Siyaram Pandey, Lasalle (CA); Jamshid Tanha, Ottawa (CA); Deyzi Gueorguieva, Windsor (CA)

(73) Assignees: National Research Council of Canada, Ottawa (CA); University of Windsor, Windsor (CA)

( * ) Notice: Subject to any disclaimer, the term of this patent is extended or adjusted under 35 U.S.C. 154(b) by 786 days.

(21) Appl. No.: 11/990,985

(22) PCT Filed: Sep. 1, 2006

(86) PCT No.: PCT/CA2006/001451
§ 371 (c)(1),
(2), (4) Date: Sep. 1, 2009

(87) PCT Pub. No.: WO2007/025388
PCT Pub. Date: Mar. 8, 2007

(65) Prior Publication Data
US 2009/0324579 A1    Dec. 31, 2009

Related U.S. Application Data

(60) Provisional application No. 60/712,831, filed on Sep. 1, 2005.

(51) Int. Cl.
| A61K 39/395 | (2006.01) |
| C07H 21/04 | (2006.01) |
| C07K 16/00 | (2006.01) |
| G01N 33/53 | (2006.01) |

(52) U.S. Cl. ... 424/130.1; 435/366; 435/7.1; 530/389.1; 536/23.53

(58) Field of Classification Search ............... 424/130.1; 435/366, 7.1; 530/389.1; 536/25.53
See application file for complete search history.

(56) References Cited

FOREIGN PATENT DOCUMENTS

| WO | WO 01/90190 A2 | 11/2001 |
| WO | WO 2004/041867 | 5/2004 |
| WO | WO 2004/003019 | * 6/2004 |
| WO | WO 2004/078146 A2 | 9/2004 |
| WO | WO 2005/044858 | 5/2005 |

OTHER PUBLICATIONS

Rudikoff et al (Proc Natl Acad Sci USA 1982 vol. 79 p. 1979).*
MacCallum et al. (J. Mol. Biol. (1996) 262:732-745)).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Verma, Nature, vol. 389, pp. 239-242, 1997.*
Rochlitz C. F. (Swiss Medicine Weekly, 131:4-9, 2001).*
Glick (Gen. Engineer. News 28(7) pp. 6 and 9 (Apr. 1, 2008)).*
EP 06 790 628.9—122 Examiner's Report.
Tomomi Kuwana, et al., BH3 Domains of BH3-Only Proteins Differentially Regulate Bax-Mediated Mitochondrial Membrane Permeabilization Both Directly and Indirectly., Molecular Cell, vol. 17, 525-535, Feb. 18, 2005.
Gueorguieva Deyzi et al: "Identification of single-domain, Bax-specific intrabodies that confer resistance to mammalian cells against oxidative-stress-induced apoptosis." The FASEB Journal: Official Publication of the Federation of American Societies for Experimental Biology Dec. 2006, vol. 20, No. 14, Dec. 2006, pp. 2636-2638, XP002574601 ISSN: 1530-6860.
Muyldermans S: "Single Domain Camel Anitbodies: Current Status" Journal of Biotechnology, Elsevier Science Publishers, Amsterdam, NL, vol. 74, No. 4, Jan. 1, 2001, pp. 277-302, XP008019929 ISSN: 0168-1656.
Supplementary European Search Report relating to EP 06 79 0628 dated Apr. 7, 2010.
Written Opinion of the International Searching Authority relating to PCT/CA2006/001451 dated Dec. 28, 2006.
International Search Report relating to PCT/CA2006/001451 dated Dec. 28, 2006.
Peter J. Adhihetty., et al., Mechanisms of Apoptosis in Skeletal Muscle., 2003, Basic Appl Myol 13 (4): 171-179.
C. Hamers-Casterman., et al., Naturally occurring antibodies devoid of light chains., Nature vol. 363, 446-448.
C. Nick Pace., et al., How to measure and predict the molar absorption coefficient of a protein., Protein Science (1995), 4:2411-2423.
David W. Colby., et al., Development of a Human Light Chain Variable Domain (VL) Intracellular Antibody Specific for the Amino Terminus of Huntingtin via Yeast Surface Display., J. Mol. Biol. (2004) 342, 901-912.
Frederico Aires da Silva., et al., Camelized Rabbit-derived VH Single-domain Intrabodies Against Vif Strongly Neutralize HIV-1 Infectivity., J. Mol. Biol. (2004) 340, 525-542.
Isaac J. Rondon., et al., Intracellular Antibodies (Intrabodies) for Gene Therapy of Infectious Diseases., Annu. Rev. Microbiol. 1997. 51:257-83.
Jamshid Tanha., et al., Phage Display Technology for Identifying Specific Antigens on Brain Endothelial Cells., From: Methods in Molecular Medicine, vol. 89, 435-450.

(Continued)

*Primary Examiner* — Lynn Bristol
(74) *Attorney, Agent, or Firm* — Cassan Maclean

(57) ABSTRACT

Single-domain anti-bodies that bind pro-apoptotic proteins Bax and caspase-3 are identified and isolated. These single-domain antibodies may be used to modulate the active of Bax and caspase-3, thereby modulating the symptoms and steps of oxidative stress and/or cell apoptosis, including Bax dimerization, mitochondrial permeabilization and the release of apoptotic proteins.

18 Claims, 14 Drawing Sheets

OTHER PUBLICATIONS

Figure 1:
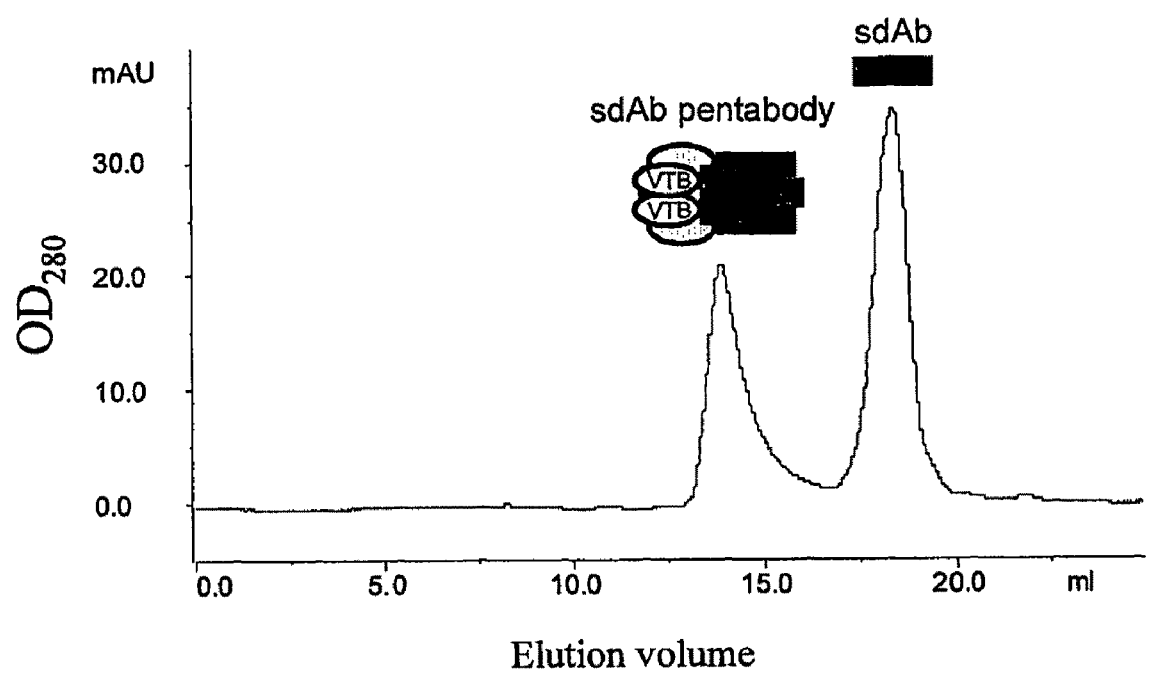

Jamshid Tanha., et al., Selection by phage display of llama conventional VH fragments with heavy chain antibody VHH properties., Journal of Immunological Methods (2002) 263 97-109.

Jianbing Zhang., et al., Pentamerization of Single-domain Antibodies from Phage Libraries: A Novel Strategy for the Rapid Generation of High-avidity Antibody Reagents., J. Mol. Biol. (2004) 335, 49-56.

Kazuhiro Nomura., et al., Mitochondrial phospholipid hydroperoxide glutathione peroxidase inhibits the release of cytochrome c from mitochondria by suppressing the peroxidation of cardiolipin in hypoglycaemia-induced apoptosis., Biochem. J. (2000) 351, 183-193.

Roland E. Kontermann., Intrabodies as therapeutic agents., R.E. Kontermann / Methods (2004) 34 163-170.

Kerrm Y.F. Yau., et al., Selection of hapten-specific single-domain antibodies from a non-immunized llama ribosome display library., Journal of Immunological Methods (2003) 281 161-175.

Kerrm Y.F. Yau., et al., Affinity maturation of a VHH by mutational hotspot randomization., Journal of Immunological Methods (2005) 297 213-224.

M. Somayajulu., et al., Role of mitochondria in neuronal cell death induced by oxidative stress; neuroprotection by Coenzyme Q10., Neurobiology of Disease (2005) 18 618-627.

Nianyu Li., et al., Mitochondrial Complex I Inhibitor Rotenone Induces Apoptosis through Enhancing Mitochondrial Reactive Oxygen Species Production., The Journal of Biological Chemistry, 2003, vol. 278, No. 10, Issue of Mar. 7, pp. 8516-8525.

N. Takeyama., et al., Role of the Mitochondrial Permeability Transition and Cytochrome c Release in Hydrogen Peroxide-Induced Apoptosis., Experimental Cell Research (2002) 274, 16-24.

Roberto Battistutta., et al., Crystal Structure and Refolding Properties of the Mutant F99S/M153TN163A of the Green Fluorescent Protein., Proteins: Structure, Function, and Genetics (2000) 41:429-437.

Santos A. Susin., et al., Molecular characterization of mitochondrial apoptosis-inducing factor., Nature vol. 397, 441-446.

F. William Sunderman., et al., Increased Lipid Peroxidation in Tissues of Nickel Chloride-Treated Rats., Annals of Clinical and Laboratory Science. vol. 15. No. 3, 229-236.

Tomoyuki Tanaka., et al., Single Domain Intracellular Antibodies: A Minimal Fragment for Direct in Vivo Selection of Antigen-specific Intrabodies., J. Mol. Biol. (2003) 331, 1109-1120.

Todd W. Miller., et al., Intrabody Applications in Neurological Disorders: Progress and Future Prospects., Molecular Therapy, Sep. 2005, vol. 12, No. 3, 394-401.

Gueorguieva et al. Identification of Unique Single Domain Antibodies (sdAb) Against Pro-Apoptic Proteins (Bax). 88th Canadian Chemistry Conference Abstracts.

Walsh et al. May 30, 2005; poster session, Abstract #413 [retrieved on Nov. 27, 2006]. Retrieved from the internet: <URL: http//csc2005.chemistry.ca/abstracts/00000381.htm>.

Zhang et al. Pentamerization of single-domain antibodies from phage libraries: a novel strategy for the rapid generation of high-avidity antibody reagents. J Mol Biol., Jan. 2, 2004;335(1):49-56, ISSN: 0022-2836.

Tanaka et al. Single domain intracellular antibodies: a minimal fragment for direct in vivo selection of antigen-specific intrabodies. J Mol Biol., Aug. 29, 2003;331(5):1109-20, ISSN: 0022-2836.

Zhang et al. Selective cytotoxicity of intracellular amyloid beta peptide 1-42 through p53 and Bax in cultured primary human neurons. J Cell Biol. Feb. 4, 2002;156(3):519-29, ISSN: 0021-9525.

* cited by examiner

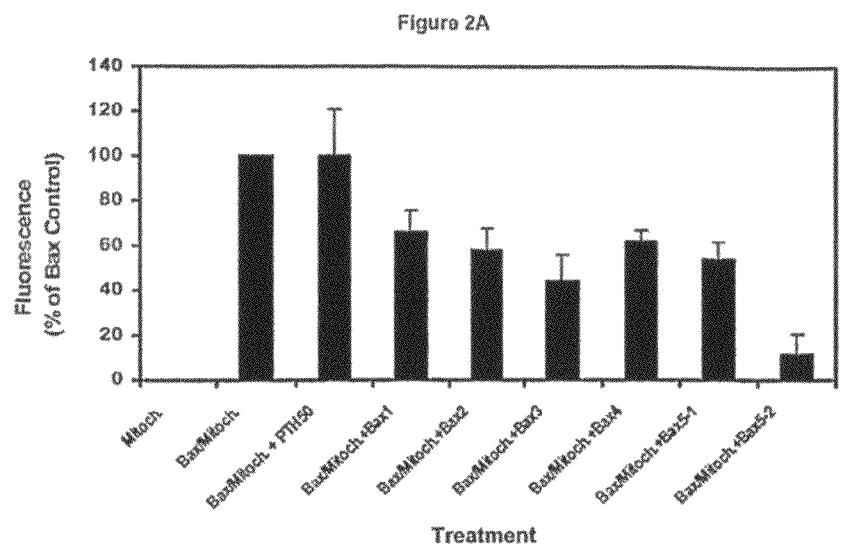
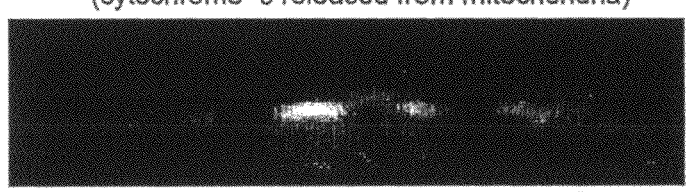
Figure 2B

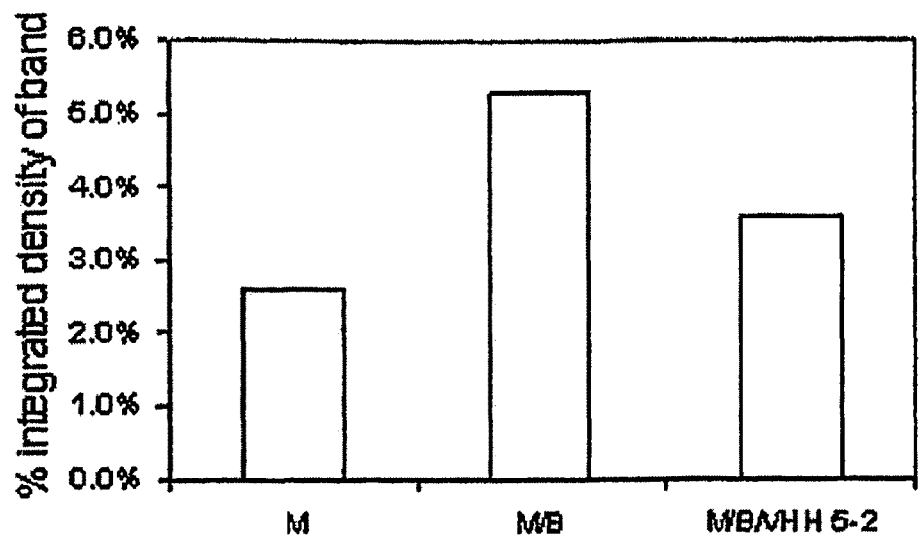
Figure 2C
Figure 3A
V$_H$H-GFP/RFP Constructs
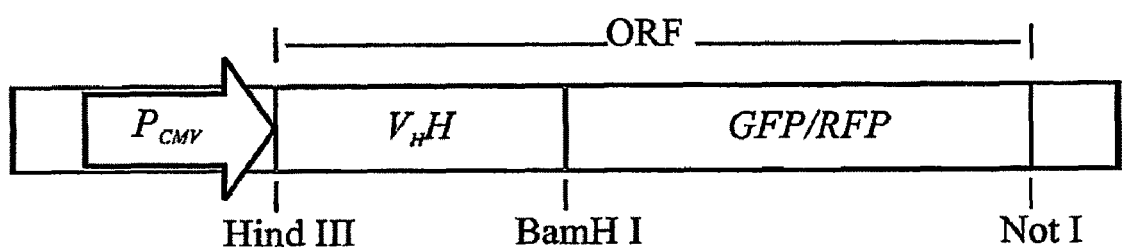

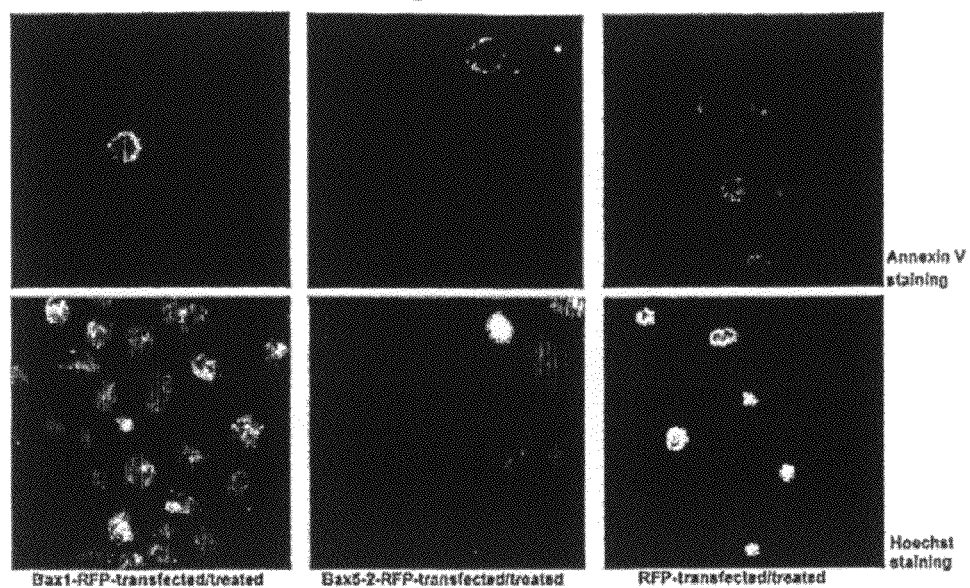
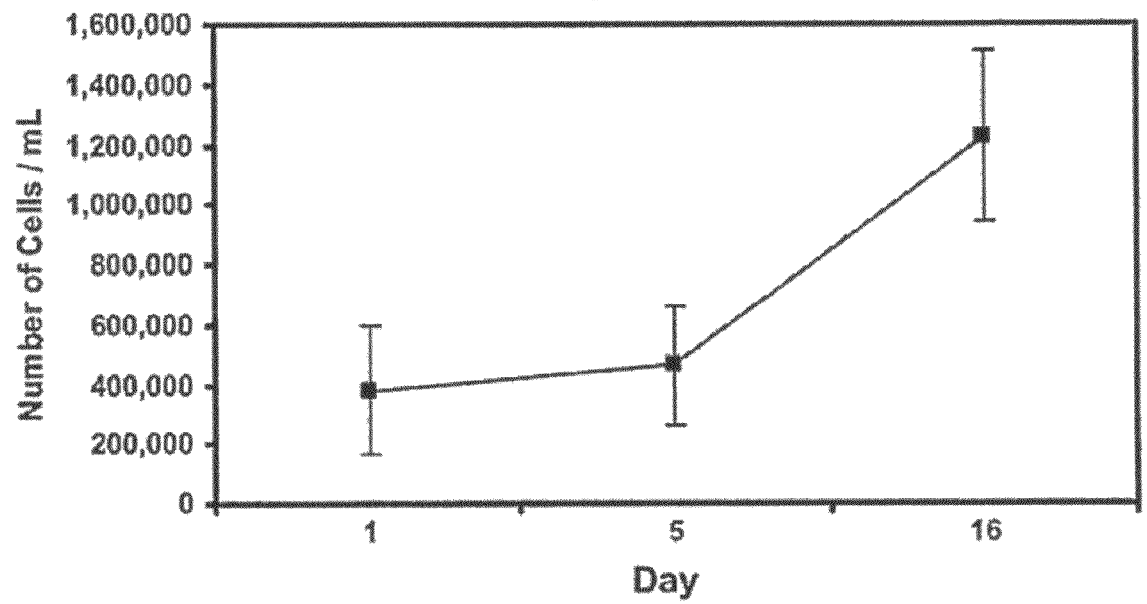

```
                        10          20        bc         30          40              50 52a53      60
Bax 2   (SEQ ID NO. 1)  DVQLQASGGGIVQAGGPLRLSCAASGRNID TYTTG WERRAPGKKREFVA          AISWSGTNTNYADSVKG
Bax 3   (SEQ ID NO. 2)  ..........S................. TFS S.AM. ......E........        ..................
Bax 1   (SEQ ID NO. 3)  ...I..S...V...DTFS R.AM. ...Q..E........                     ...RG.GSQF....AG.
Bax 5-2 (SEQ ID NO. 4)  .......S.....TNS W.SM. ...Q..E........                       ....N.DAIY.T....
Bax 4   (SEQ ID NO. 5)  S..P..S.......VVY.I...... ...Q.....D..E.S                   C..SR.-S.S......
Bax 5-1 (SEQ ID NO. 6)  ...........DS...FAYN R.NM. ...Q..ME........                  .FR.ITGT.Q..N.A..

70        80 82a bc83      90          100      a-j    101
Bax2                    RFTISRDNAKNTMYLQMNRLIAPEDTAVYYCAA TSTRTYYTTTSRSNEIVY          WGQGTQVTVSS
Bax3                    ..........V........S.S..........  DGQI.F.TARTA.A--.G.         ..........
Bax1                    ......T..V........S.K......I..... HAAAFTEAAHIPG---.E.         ..........
Bax5-2                  ...........V........S.KS......... VFGSSCNVLLD----FGS          R.........
Bax4                    ..RM...G.KMV........S.K.......... ..........                  ..........
Bax5-1                  ......V........S.K.K............. DPRV.FNVNE-----FD.          ..R.......
```

Fig.14

(A) Casp1 (SEQ ID NO.: 7)

D V Q L Q A S G G G L V Q P G G S L R L S C A A S G S L S R <u>I T V M G</u> W Y R Q A P G K Q R E L V A <u>I I T S S G G T N Y A D S V K G</u> R F T I S R D N A K N T V Y L Q M N S L K P E D T A V Y Y C L A <u>A R G Y D R Y</u> W G R G T Q V T V S S (B) Casp2 (SEQ ID NO.: 8)

D V Q L Q A S G G G L V Q A G G S L R L S C A A S T N I F R <u>D K F M A</u> W Y R Q A P G K Q R E L V A <u>S I T T G G R T D Y A D S V K G</u> R F T I S R D N T K D T M Y L Q M N S L K P E D T A V Y Y C A G <u>F L G R T Y</u> W G Q G T Q V T V S S

SEQUENCE LISTING

<160> NUMBER OF SEQ ID NOS: 17

<210> SEQ ID NO 1
<211> LENGTH: 127
<212> TYPE: PRT
<213> ORGANISM: Lama glama

<400> SEQUENCE: 1

Asp Val Gln Leu Gln Ala Ser Gly Gly Gly Leu Val Gln Ala Gly Gly
1               5                   10                  15

Pro Leu Arg Leu Ser Cys Ala Ala Ser Gly Arg Asn Ile Asp Thr Tyr
            20                  25                  30

Thr Thr Gly Trp Phe Arg Arg Ala Pro Gly Lys Lys Arg Glu Phe Val
        35                  40                  45

Ala Ala Ile Ser Trp Ser Gly Thr Asn Thr Asn Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Arg Leu Ala Pro Glu Asp Thr Ala Val Tyr Tyr Cys
                85                  90                  95

Ala Ala Thr Ser Thr Arg Thr Tyr Tyr Tyr Thr Thr Ser Arg Ser Asn
            100                 105                 110

Glu Tyr Val Tyr Trp Gly Gln Gly Thr Gln Val Thr Val Ser Ser
        115                 120                 125

<210> SEQ ID NO 2
<211> LENGTH: 127
<212> TYPE: PRT
<213> ORGANISM: Lama glama

<400> SEQUENCE: 2

Asp Val Gln Leu Gln Ala Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Arg Ala Pro Gly Lys Glu Arg Glu Phe Val
        35                  40                  45

Ala Ala Ile Ser Trp Ser Gly Thr Asn Thr Asn Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Arg Leu Ala Pro Glu Asp Thr Ala Val Tyr Tyr Cys
                85                  90                  95

Ala Ala Thr Ser Thr Arg Thr Tyr Tyr Tyr Thr Thr Ser Arg Ser Asn
            100                 105                 110

Glu Tyr Val Tyr Trp Gly Gln Gly Thr Gln Val Thr Val Ser Ser
        115                 120                 125

<210> SEQ ID NO 3
<211> LENGTH: 126
<212> TYPE: PRT
<213> ORGANISM: Lama glama

<400> SEQUENCE: 3

Asp Val Gln Leu Gln Ala Ser Gly Gly Gly Leu Val Gln Ile Gly Gly
1               5                   10                  15

Ser Leu Arg Leu Ser Cys Val Ala Ser Gly Asp Thr Phe Ser Arg Tyr

```
                    20                  25                  30
Ala Met Gly Trp Phe Arg Gln Ala Pro Gly Lys Glu Arg Glu Phe Val
            35                  40                  45

Ala Ala Ile Ser Arg Gly Gly Gly Ser Gln Phe Tyr Ala Asp Ser Ala
        50                  55                  60

Gly Gly Arg Phe Thr Ile Ser Arg Asp Asn Ala Lys Asn Thr Val Tyr
 65                  70                  75                  80

Leu Gln Met Asn Ser Leu Ser Pro Glu Asp Thr Ala Val Tyr Tyr Cys
                85                  90                  95

Ala Ala Asp Gly Gln Ile Thr Phe Tyr Thr Arg Thr Ala Ser Ala
            100                 105                 110

Tyr Gly Tyr Trp Gly Gln Gly Thr Gln Val Thr Val Ser Ser
            115                 120                 125

<210> SEQ ID NO 4
<211> LENGTH: 125
<212> TYPE: PRT
<213> ORGANISM: Lama glama

<400> SEQUENCE: 4

Asp Val Gln Leu Gln Ala Ser Gly Gly Gly Leu Val Gln Ala Gly Gly
  1               5                  10                  15

Ser Leu Arg Leu Ser Cys Ala Ala Ser Gly Arg Thr Asn Ser Trp Tyr
            20                  25                  30

Ser Met Gly Trp Phe Arg Gln Ala Pro Gly Lys Glu Arg Glu Phe Val
            35                  40                  45

Ala Ala Ile Ser Trp Asn Gly Asp Ala Ile Tyr Tyr Thr Asp Ser Val
        50                  55                  60

Lys Gly Arg Phe Thr Ile Ser Arg Asp Asn Thr Lys Asn Thr Val Tyr
 65                  70                  75                  80

Leu Gln Met Asn Ser Leu Lys Pro Glu Asp Thr Ala Val Tyr Ile Cys
                85                  90                  95

Ala Ala His Ala Ala Ala Phe Thr Glu Ala Ala His Ile Pro Gly Tyr
            100                 105                 110

Glu Tyr Trp Gly Gln Gly Thr Gln Val Thr Val Ser Ser
            115                 120                 125

<210> SEQ ID NO 5
<211> LENGTH: 122
<212> TYPE: PRT
<213> ORGANISM: Lama glama

<400> SEQUENCE: 5

Asp Val Gln Leu Gln Ala Ser Gly Gly Gly Ser Val Gln Pro Gly Gly
  1               5                  10                  15

Ser Leu Arg Leu Ser Cys Ala Ala Ser Gly Val Val Tyr Asp Tyr Trp
            20                  25                  30

Thr Ile Gly Trp Phe Arg Gln Ala Pro Gly Lys Asp Arg Glu Glu Val
            35                  40                  45

Ser Cys Ile Ser Ser Arg Gly Ser Thr Ser Tyr Ala Asp Ser Val Lys
        50                  55                  60

Gly Arg Phe Arg Met Ser Arg Asp Asn Gly Lys Lys Met Val Tyr Leu
 65                  70                  75                  80

Gln Met Asn Ser Leu Lys Ser Glu Asp Thr Ala Val Tyr Tyr Cys Ser
                85                  90                  95

Ala Val Phe Gly Ser Ser Cys Asn Val Leu Leu Asp Phe Gly Ser Arg
            100                 105                 110
```

```
Gly Gln Gly Thr Gln Val Thr Val Ser Ser
        115                 120

<210> SEQ ID NO 6
<211> LENGTH: 122
<212> TYPE: PRT
<213> ORGANISM: Lama glama

<400> SEQUENCE: 6

Asp Val Gln Leu Gln Ala Ser Gly Gly Gly Leu Val Gln Ala Gly Asp
 1               5                  10                  15

Ser Leu Arg Leu Ser Cys Ala Ala Ser Gly Phe Ala Tyr Asn Arg Tyr
            20                  25                  30

Asn Met Gly Trp Phe Arg Gln Ala Pro Gly Met Glu Arg Glu Phe Val
        35                  40                  45

Ala Ala Phe Arg Trp Ile Thr Gly Thr Thr Gln Tyr Ala Asn Ser Ala
    50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Lys Asp Thr Ala Val Tyr Tyr Cys
                85                  90                  95

Ala Ala Asp Pro Arg Val Thr Phe Asn Val Asn Glu Phe Asp Tyr Trp
            100                 105                 110

Gly Arg Gly Thr Gln Val Thr Val Ser Ser
        115                 120

<210> SEQ ID NO 7
<211> LENGTH: 115
<212> TYPE: PRT
<213> ORGANISM: Lama glama

<400> SEQUENCE: 7

Asp Val Gln Leu Gln Ala Ser Gly Gly Gly Leu Val Gln Pro Gly Gly
 1               5                  10                  15

Ser Leu Arg Leu Ser Cys Ala Ala Ser Gly Ser Leu Ser Arg Ile Thr
            20                  25                  30

Val Met Gly Trp Tyr Arg Gln Ala Pro Gly Lys Gln Arg Glu Leu Val
        35                  40                  45

Ala Ile Ile Thr Ser Ser Gly Gly Thr Asn Tyr Ala Asp Ser Val Lys
    50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Leu
                85                  90                  95

Ala Ala Arg Gly Tyr Asp Arg Tyr Trp Gly Arg Gly Thr Gln Val Thr
            100                 105                 110

Val Ser Ser
    115

<210> SEQ ID NO 8
<211> LENGTH: 114
<212> TYPE: PRT
<213> ORGANISM: Lama glama

<400> SEQUENCE: 8

Asp Val Gln Leu Gln Ala Ser Gly Gly Gly Leu Val Gln Ala Gly Gly
 1               5                  10                  15

Ser Leu Arg Leu Ser Cys Ala Ala Ser Thr Asn Ile Phe Arg Asp Lys
```

```
                  20                  25                  30

Phe Met Ala Trp Tyr Arg Gln Ala Pro Gly Lys Gln Arg Glu Leu Val
            35                  40                  45

Ala Ser Ile Thr Thr Gly Gly Arg Thr Asp Tyr Ala Asp Ser Val Lys
    50                  55                  60

Gly Arg Phe Thr Ile Ser Arg Asp Asn Thr Lys Asp Thr Met Tyr Leu
65                  70                  75                  80

Gln Met Asn Ser Leu Lys Pro Glu Asp Thr Ala Val Tyr Tyr Cys Ala
                85                  90                  95

Gly Phe Leu Gly Arg Thr Tyr Trp Gly Gln Gly Thr Gln Val Thr Val
            100                 105                 110

Ser Ser

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 9

His His His His His
  1               5

<210> SEQ ID NO 10
<211> LENGTH: 381
<212> TYPE: DNA
<213> ORGANISM: Lama glama

<400> SEQUENCE: 10
gatgtgcagc tgcaggcgtc tgggggagga ttggtgcagg ctgggggccc tctgagactc      60
tcctgtgcag cctctggacg caacatcgat acatatacca cgggctggtt ccgccgggct     120
ccagggaaga agcgcgaatt tgtggcagct attagctgga gtggtactaa cacaaactat     180
gcagactccg tgaagggtcg attcaccatc tccagagaca cgccaagaa cacgatgtat      240 ctgcaaatga acaggttggc gcctgaggac acggccgttt attactgtgc agccacctct     300
actcgtactt actactacac acatctaggg agtaatgagt atgtctactg gggccagggg     360
acccaggtca ccgtctcctc g                                               381

<210> SEQ ID NO 11
<211> LENGTH: 381
<212> TYPE: DNA
<213> ORGANISM: Lama glama

<400> SEQUENCE: 11
gatgtgcagc tgcaggcgtc tgggggagga ttggtgcagg ctgggggctc tctgagactc      60
tcctgtgcag cctctggacg caccttcagt agctatgcca tgggctggtt ccgccgggct     120
ccagggaagg agcgcgaatt tgtggcagct attagctgga gtggtactaa cacaaactat     180
gcagactccg tgaagggtcg attcaccatc tccagagaca cgccaagaa cacgatgtat      240 ctgcaaatga acaggttggc gcctgaggac acggccgttt attactgtgc agccacctct     300
actcgtactt actactacac acatctaggg agtaatgagt atgtctactg gggccagggg     360
acccaggtca ccgtctcctc g                                               381

<210> SEQ ID NO 12
<211> LENGTH: 378
```

```
<212> TYPE: DNA
<213> ORGANISM: Lama glama

<400> SEQUENCE: 12
gatgtgcagc tgcaggcgtc tgggggaggt ttggtgcaga ttgggggctc tctgagactc    60
tcctgtgtag cctctggaga caccttcagt cgatatgcga tgggttggtt ccgccaggcc   120
ccagggaagg agcgtgagtt tgtagcggcg attagtcggg gtggtggaag ccaattctac   180
gcggactccg cgggcggccg attcaccatc tccagagaca acgccaagaa cacggtgtat   240
ctgcaaatga acagcctgag tcctgaggat acggccgttt attactgtgc agcagatggg   300
caaattacct tttacaccgc acggaccgcc tccgcgtatg ctattgggg ccaggggacc    360 caggtcaccg tctcctcg                                                 378

<210> SEQ ID NO 13
<211> LENGTH: 375
<212> TYPE: DNA
<213> ORGANISM: Lama glama

<400> SEQUENCE: 13
gatgtgcagc tgcaggcgtc tgggggagga ttggtccagg ctgggggctc tctgaggctc    60
tcctgtgcag cctctggacg caccaatagt tggtattcca tgggctggtt tcgccaggct   120
cccgggaagg agcgggagtt tgtagccgct attagttgga atggcgatgc tatatactac   180
acagactctg tcaagggccg attcaccatc tccagagaca ataccaaaaa cactgtgtac   240
ctgcaaatga acagcctgaa acctgaggac acggccgttt atatctgtgc agcacatgcg   300
gctgcattta cagaagcggc ccatatccct gggtatgagt actggggcca ggggacccag   360
gtcaccgtct cctcg                                                    375

<210> SEQ ID NO 14
<211> LENGTH: 366
<212> TYPE: DNA
<213> ORGANISM: Lama glama

<400> SEQUENCE: 14
gatgtgcagc tgcaggcgtc tgggggaggc tcggtgcagc ctgggggtc tctgagactc     60 tcttgtgcag cctctggagt ggtttacgac tattggacca taggctggtt ccgccaggcc   120
ccagggaagg atcgcgagga ggtctcgtgt attagtagta gagggagtac atcatatgca   180
gactccgtga agggccgatt ccgcatgtcc cgtgacaatg caagaagat ggtgtatctg     240 caaatgaaca gcctgaaatc cgaggacacg gccgtttatt attgctcagc ggtattcggt   300
agtagctgca acgtcctcct tgactttggt tcccggggcc aggggaccca ggtcaccgtc   360
tcctcg                                                              366

<210> SEQ ID NO 15
<211> LENGTH: 366
<212> TYPE: DNA
<213> ORGANISM: Lama glama

<400> SEQUENCE: 15
gatgtgcagc tgcaggcgtc tgggggagga ttggtgcagg ctggggactc tctgagactc    60
tcctgtgcag cctctggatt cgcctacaat aggtataaca tgggctggtt ccgccaggct   120
ccagggatgg agcgtgaatt tgtagcagcg tttaggtgga ttactggtac cacacagtat   180
gcaaactccg cgaagggccg attcaccatc tccagagaca acgccaagaa cacggtgtat   240
ctgcaaatga acagcctgaa acctaaggac acggccgttt attactgtgc agcagatccg   300
```

```
aggg tgactt tcaatgttaa cgagtttgac tattggggcc gggggaccca ggtcaccgtc    360
tcctcg                                                               366

<210> SEQ ID NO 16
<211> LENGTH: 345
<212> TYPE: DNA
<213> ORGANISM: Lama glama

<400> SEQUENCE: 16
gatgtgcagc tgcaggcgtc tgggggaggc ttggtgcagc ctgggggtc tctgagactc      60 tcctgtgcag cctctggaag cctctccagg atcacggtca tgggctggta ccgccaggct   120
ccagggaagc agcgcgagtt ggtcgcaatt attactagta gtggcggcac aaactatgca   180
gactccgtga agggccgatt caccatctcc agagacaacg ccaagaacac ggtgtatctg   240
caaatgaaca gcctgaaacc tgaggacaca gccgtgtatt actgcttagc agctagggc    300 tatgaccggt actggggccg ggggacccag gtcaccgtct cctca                   345

<210> SEQ ID NO 17
<211> LENGTH: 342
<212> TYPE: DNA
<213> ORGANISM: Lama glama

<400> SEQUENCE: 17
gatgtgcagc tgcaggcgtc tggaggaggc ttggtgcagg ctgggggtc tctgcgactc      60 tcctgtgcag cctctacaaa tatcttcaga gacaagttca tggcctggta ccgccaggct   120
ccagggaagc agcgcgaatt ggtcgcgtcg attactactg tggtaggac agactatgca    180 gactccgtga agggccgatt caccatctcc agagacaaca ccaaggacac gatgtatctg   240
caaatgaaca gcctgaaacc tgaggacaca gccgtctatt actgtgcggg tttcttgggg   300
agaacctact ggggccaggg gacccaggtc accgtctcct ca                      342
```

US 8,361,462 B2

ANTI-APOPTOTIC PROTEIN ANTIBODIES

RELATED APPLICATIONS

This is a national entry application claiming the benefit of PCT Application No. PCT/CA2006/001451, which claims priority to U.S. Provisional Application No. 60/712,831.

FIELD OF THE INVENTION

The invention relates to antibodies and fragments thereof which target proteins with pro-apoptotic function, and methods for using such antibodies.

BACKGROUND OF THE INVENTION

Programmed cell death or apoptosis is a physiological process essential for normal development and tissue homeostasis. Cell death mechanisms are protective measures for organisms which ensure the removal of unnecessary, damaged or potentially dangerous cells. However, any deregulation or inappropriate induction of this process leads to the loss of healthy cells, causing diseases. In particular, cell death in post-mitotic tissues such as the brain and heart in adult organisms results in functional compromise, as is the case in Alzheimer's disease, Parkinson's disease and stroke. Cell death induced by oxidative stress has been shown to be involved in the development of these pathologies. Although the exact mechanism of cell death induced by oxidative stress is still not known, mitochondria have been shown to play a central role in this process. Mitochondrial events such as opening of the permeability transition pores, mitochondrial membrane potential collapse and release of pro-apoptotic factors such as cytochrome c and/or apoptosis-inducing factors trigger the cascade of events leading to execution of apoptosis.

Bax is a 24 kDa protein of the Bcl-2 family with pro-apoptotic function. It normally resides in cytosol and translocates to mitochondria upon induction of apoptosis and it plays a key role in destabilizing mitochondria. Translocation of Bax to mitochondria followed by a conformational change (mitochondrial permeabilization) in association with Bid leads to the release of cytochrome c, apoptosis-inducing factor and caspase-9, a cysteine protease, which start the execution phase of apoptosis. Bax has been implicated in neuronal cell death during development and ischemia.

Caspase-3 is normally present in a dormant form. Once activated, it plays a role in the disintegration of various key proteins in the cell, including the activation of an endonuclease which fragments cell DNA.

Intrabodies to apoptotic proteins with inhibitory action would be useful in the treatment of neurodegenerative disorders, in addition to being valuable tools for studying apoptosis. The efficacy of intrabodies critically depends on their stability. In the reducing environment of the cytoplasm, intrabodies cannot form their stabilizing disulfide linkage(s), so only those which are of sufficient stability can tolerate the absence of the disulfide linkage and be expressed in functional form. Traditionally, single chain Fvs (single chain Fvs, or "scFvs" consist of an antibody heavy chain variable domain, $V_H$, and a light chain variable domain, $V_L$, joined together by a linker) have been used as intrabodies (Kontermann, R. E., 2004). More recently, the feasibility of three types of single-domain antibodies (sdAbs), $V_L$s, $V_H$s and $V_H$Hs ($V_H$Hs derived from camelid heavy chain antibodies (Hamers-Casterman C. et al., 1993), as intrabodies has also been demonstrated. While offering a comparable affinity, sdAbs have higher stability, solubility and expression level than scFvs and thus, are more efficacious as intrabodies (Tanaka, T. et al., 2003; Aires da Silva, F. et al., 2004; Colby, D. W. et al., 2004) Intrabodies can be derived from monoclonal antibodies or antibody display libraries, e.g., antibody phage display libraries (Rondon, I. J. et al., 1997; Miller, T. W. et al., 2005).

DETAILED DESCRIPTION OF THE DRAWINGS

FIG. 1. Superdex 200 size exclusion chromatogram showing the separation of a monomeric anti-Bax sdAb from a pentameric one (pentabody). In the sdAb pentabody, VTB represents the verotoxin B subunit, the pentamerization domain. The expected molecular weight of the pentabody is 118 kDa.

FIG. 2. A. In vitro protection of mitochondria by anti-Bax $V_H$HS. Measurement of ROS generation in isolated mitochondria (Mitoch). Isolated mitochondria were incubated with Bax either in the presence or absence of different $V_H$Hs in a reaction buffer. ROS generation was measured as described below. ROS generated by Bax alone was taken as 100%. Different $V_H$Hs inhibited ROS production caused by Bax to different degrees with the best effect seen with Bax5-2 $V_H$H. The standard error shown as error bars was calculated using Microsoft Excel program and the data obtained from five separate experiments. P values were calculated using Statistica Application Program for Windows 95, where p values less than 0.05 were assumed to be significantly different. Compared to the mitochondrial/Bax (M/B) the ROS decrease was significant in fractions containing Bax2 or Bax5-2 with p values under 0.05, while fractions containing the irrelevant $V_H$H$V_H$H or Bax1 did not show a statistically significant decrease in ROS generation (p-values above 0.05). B. Limited leakage of pro-apoptotic proteins from mitochondria in presence of anti-Bax $V_H$HS. Cytochrome c retention and release from mitochondria was detected by Western blot in the pellet and supernatant fractions (latter shown) of the reaction mixture containing isolated mitochondria incubated in the presence or absence of Bax with or without $V_H$H. Samples containing Bax5-2 $V_H$H and incubated with Bax (lane 3) lead to a decrease in cytochrome c release in the supernatant fraction than the control fraction containing mitochondria and Bax only (lane 2) indicating a decrease in mitochondrial membrane stabilization due to the presence of the anti-Bax intrabody. C. Quantification of band intensity for cytochrome c release was calculated using Chemilmanager V5.5 program based on the integrated density value for each band, indicating that the greatest amount of cytochrome c was released by the fraction containing mitochondria and Bax alone (M/B). $V_H$H 5-2=Bax5-2

FIG. 3. A Cloning and expression of $V_H$Hs in mammalian cells. Schematic diagram shows a $V_H$H expression construct in mammalian vectors in fusion with green fluorescent protein, GFP or red fluorescent protein, RFP. The heptapeptide DPPVATM links the C-terminus of the $V_H$H to the N-terminus of the GFP or RFP. The parent vector alone with no $V_H$H, expresses the fluorescent-proteins; For the expression of $V_H$H alone, the $V_H$H gene was cloned between Hind III and Not I restriction endonuclease sites. ORF, open reading frame, denoting the mature translated product; $P_{CMV}$, cytomegalovirus promoter; $V_H$H, $V_H$H gene; GFP, GFP gene; RFP, RFP gene. B. Confirming the formation of a stable cell line expressing anti-Bax intrabodies. Western blot analysis of expression of GFP-$V_H$H genes in mammalian cells: total protein extract from cells transfected with GFP gene (~30 kDa, lane 1) or each of various $V_H$H-GFP genes (~40 kDa, lane 2-4) were resolved on SDS-PAGE, transferred to nitrocellulose membrane and immunoblotted using anti-GFP antibody as described herein. Numbers on the left side of the figure show the locations of the molecular weight markers. C. Fluorescent microscopy showing the expression of Bax4-RFP in a stable cell line. SHSY-5Y cells were transected with $V_HH$ expression vectors, creating three groups of unique stable cell lines expressing the six anti-Bax $V_H$Hs in fusion with either RFP (shown here) or GFP or in absence of a fusion protein. Geneticin was supplemented in order to select only positively transfected cells. Here RFPs were used as markers for $V_H$H expression, with positively transfected cells staining red.

Figure 4:
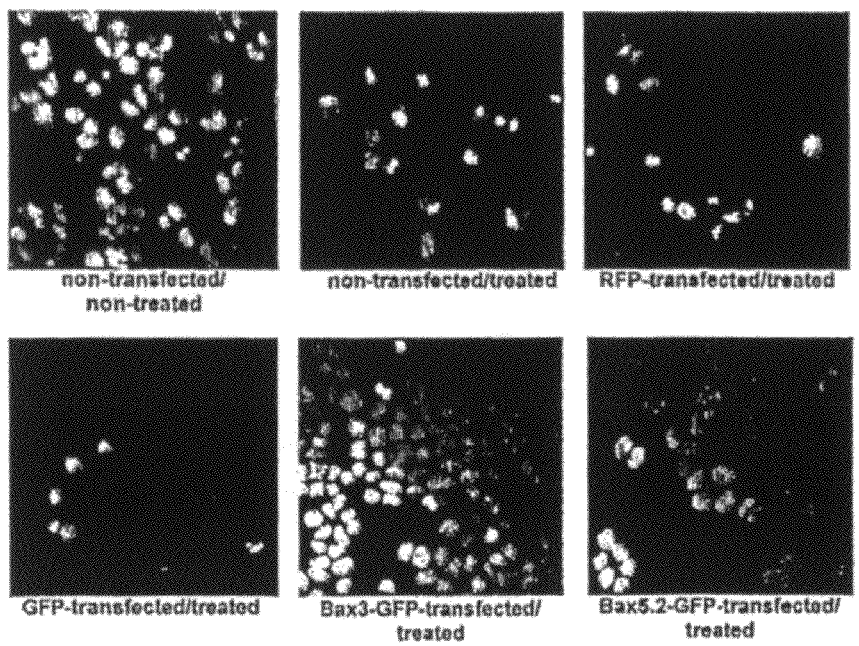

FIG. 4 Monitoring nuclear morphology after oxidative stress. Nuclei of control cell lines and those expressing anti-Bax $V_H$Hs were monitored using Hoechst reagent to detect brightly stained, condensed nuclei indicative of apoptotic cells. All culture plates containing anti-Bax $V_H$H-expressing cells show very few apoptotic nuclei (Bax 3 and Bax5-2 are shown) comparable to non-transfected/non-treated SHSY-5Y. In contrast, control SHSY-5Y cell lines (non-transfected, RFP only or GFP only) exposed to equal treatment have a greater number of apoptotic condensing nuclei, in fact at this time the majority of these cells are completely dead and lifted off the culture plates and thus not captured in the shown fields.

Figure 5:
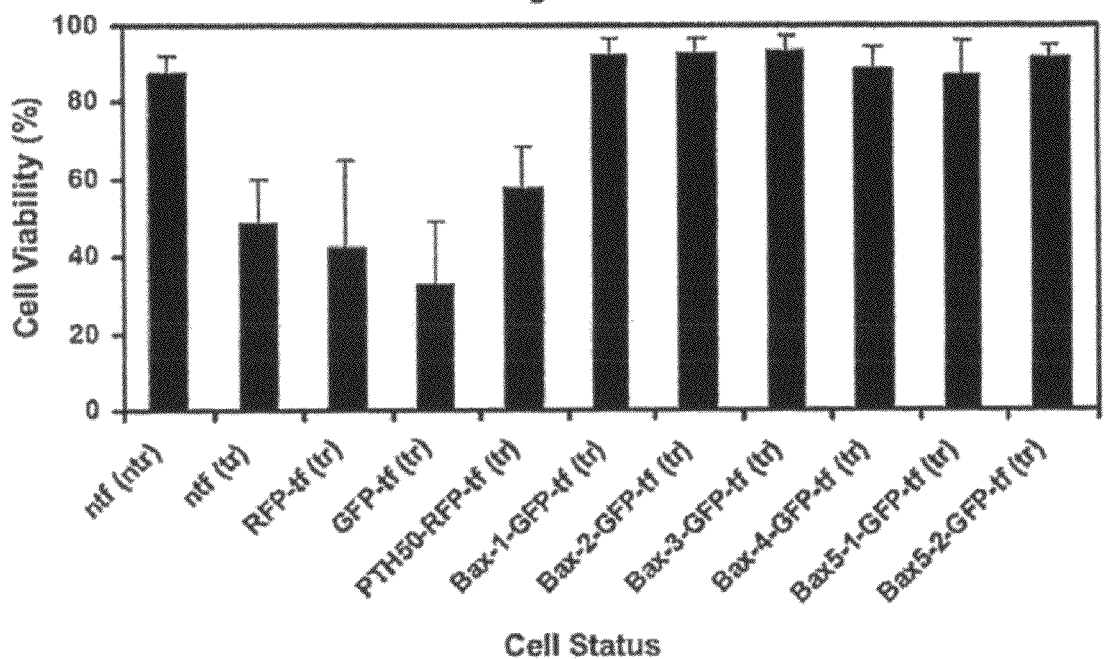

FIG. 5 Quantifying cell viability following oxidative stress. Cell lines transfected (tf) with anti-Bax $V_H$H-GFPs were treated (tr) with oxidative stress (100 μM $H_2O_2$ for 1 h). Control cells included non-transfected/non-treated cells, ntf (ntr), non-transfected/treated cells, ntf (tr), RFP-transfected/treated cells, RFP-tf (tr), GFP-transfected/treated cells, GFP-tf (tr) and PTH50-RFP-tf (tr) cells. After 24 h cultures were stained with Hoechst reagent (as described in FIG. 4). Healthy and apoptotic nuclei from three separate experiments were counted using 6-10 fields/cell line/experiment; and the number of healthy cells was plotted as a percentage of all the cells counted as Cell Viability. SHSY-5Y cells transfected with each of the six anti-Bax $V_H$Hs (fused with GFP or RFP) show strong resistance to apoptosis which was significantly different from all the control treated cell lines (ntf(tr), GFP-tf(tr), RFP-tf(tr), PTH50-tf(tr)) expressing p values less than 0.05.

FIG. 6. Detecting early phase apoptosis through Annexin V staining. Annexin V was used to monitor plasma membrane flipping resulting in a green fluorescent outline of apoptotic cells. After the described treatment, cells lacking $V_H$H genes showed a greater proportion of annexin V staining than the ones expressing the $V_H$Hs (Bax1 and Bax5-2 $V_H$Hs are shown). Hoechst staining also shows a greater proportion of healthy nuclei in SHSY-5Y cells transfected with the anti-Bax $V_H$H than those transfected with RFP protein only.

FIG. 7. Post-oxidative stress cell division in cells expressing anti-Bax $V_H$HS. Growth rates of the protected cells containing all six $V_H$Hs (Bax5-2-GFP-transfected cells are shown) remain unaffected after treatment with 200 μM $H_2O_2$ for 1 h. Cells were trypsinized and plated on fresh dishes 48 h after the $H_2O_2$ treatment and cell numbers were counted at day 1, 5 and 16 using trypan blue staining and a hemocytometer.

Figure 8:
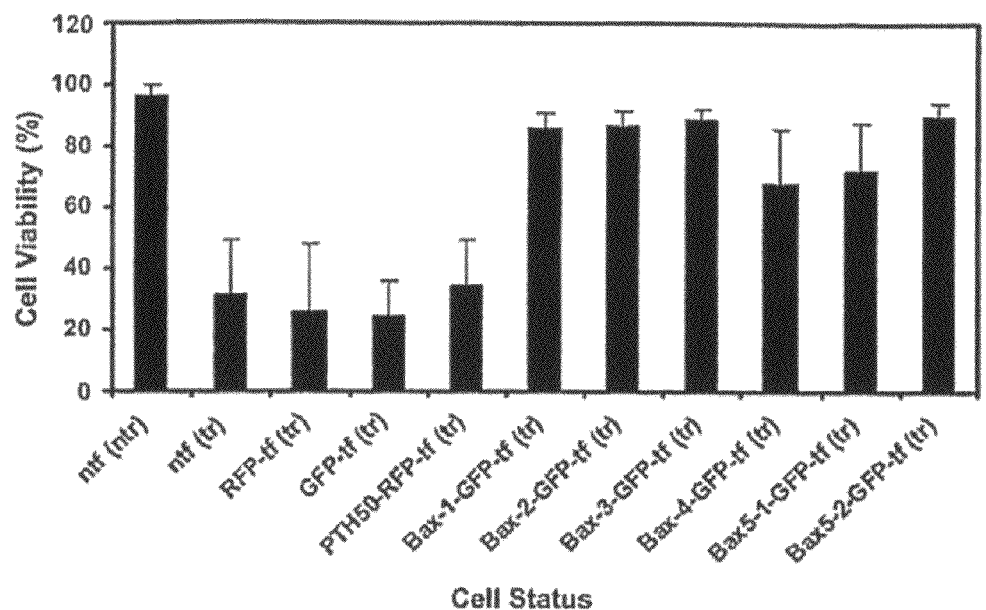

FIG. 8. Quantifying cell viability post increased oxidative stress. Twelve stable cell lines expressing the six anti-Bax $V_H$Hs in fusion with GFP and RFP were all exposed to treatment with 200 μM $H_2O_2$ for 1 h and were monitored after 24 h. Cell viability was calculated showing a significant survival rate in cells expressing Bax3 or Bax5-2 $V_H$Hs (no significant viability change was noted between each fusion protein used). Non-transfected cells (ntf) or cells transfected only with RFP, GFP or an irrelevant $V_H$H (PTH50), showed very poor survival rate (20-30%) when treated (tr) indicating that expression of anti-Bax $V_H$H is necessary for resistance to oxidative stress. ntr, non-treated. These results were further confirmed and shown to be statistically significant by calculating the p values. The cell viability for each of the anti-Bax $V_H$Hs was compared against each of the control treated cell lines, showing p values less than 0.05 and each of the control cell lines were also shown to be statistically different from the non-treated/transfected cells (p<0.05). ntr, non-treated.

Figure 9:
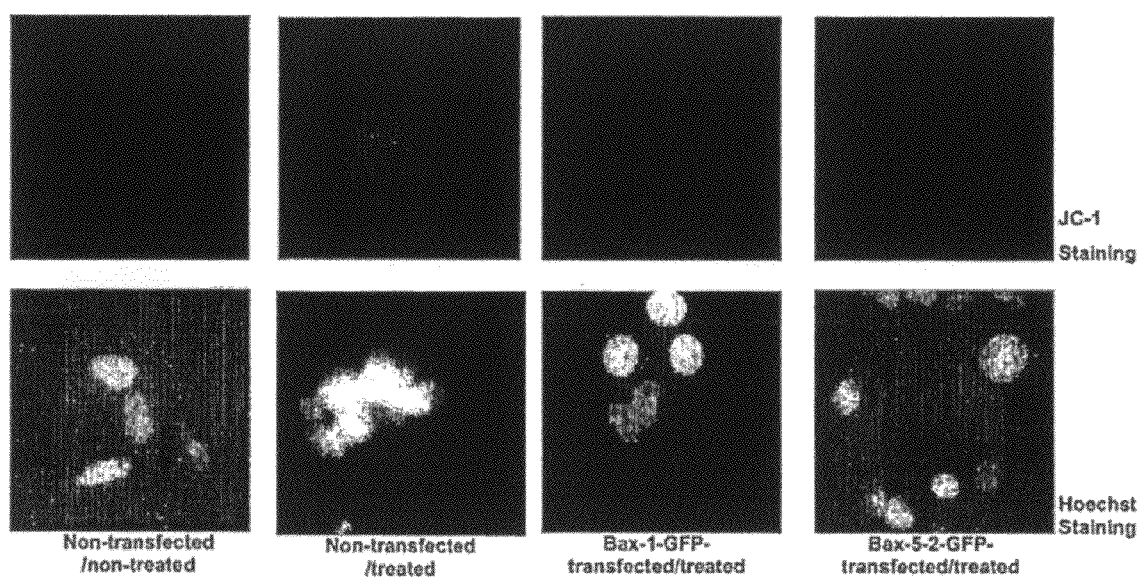

FIG. 9. Anti-Bax $V_H$H expression causes mitochondrial stabilization following oxidative stress. Nuclear and mitochondrial staining was performed with Hoechst and JC-1 dyes, respectively, 24 h after the indicated treatment. Cells expressing all six anti-Bax $V_H$Hs in fusion with GFP show healthy nuclei comparable to non-treated/non-transfected cells (Bax1 and Bax5-2 $V_H$Hs are shown). Mitochondrial membrane destabilization was monitored using JC-1. Healthy cells containing mitochondria with intact membrane potential show red fluorescence as in non-treated cells and cells containing $V_H$H (not done with RFP-transfected cells since the red would show from both the RFP and healthy mitochondria).

Figure 10:
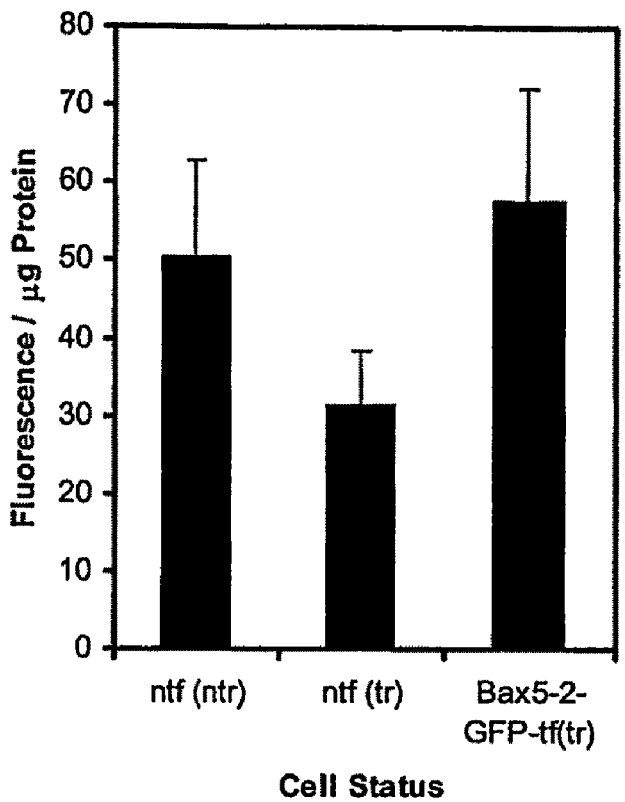

FIG. 10 Mitochondrial membrane potential is protected in the presence of anti-Bax $V_H$HS. The mitochondrial membrane potential was measured using a cationic dye which accumulates in healthy mitochondria and can be detected quantitatively using a fluorescence plate reader. Non-treated SHSY-5Y cells, ntf (ntr), with healthy mitochondria expressed high fluorescence/μg protein readings similar to the cells expressing Bax5-2 $V_H$H and treated with 100 μM $H_2O_2$/1 h. Conversely, non-transfected SHSY-5Y, ntf (tr), exposed to the same treatment showed a significant decrease in fluorescence indicative of destabilized mitochondrial membrane potentials.

Figure 11:
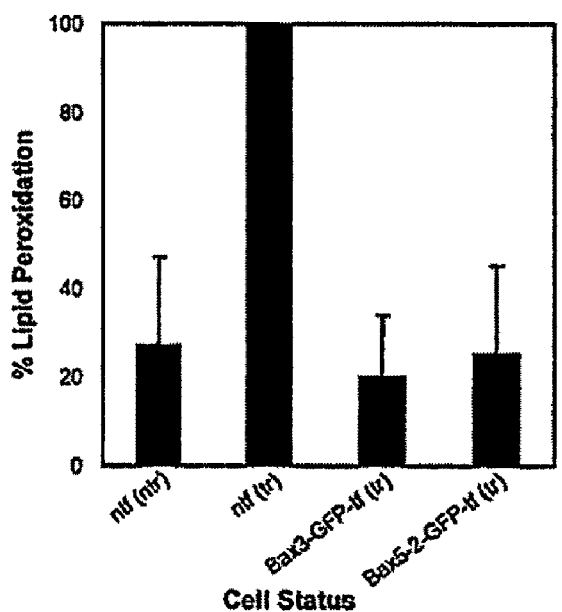

FIG. 11. Anti-Bax $V_H$Hs prevent lipid peroxidation after oxidative stress. Lipid peroxidation was monitored in cells treated with 100 μM $H_2O_2$ for 1 h. Cells expressing all six anti-Bax $V_H$Hs (Bax 3 and Bax5-2 are shown) showed a drastic decrease of lipid peroxidation compared to the control cells (non-transfected/treated, ntf (tr)) which were taken as 100% peroxidation. Lipid peroxidation levels of the transfected cells (tf) were similar to that of non-transfected/non-treated (ntf (ntr)) cells. Compared to the ntf (ntr) cells, the ntf (tr) and PTH50-transfected (tr) cells the lipid peroxidation percentages in these latter cell lines were shown to be statistically different (p<0.05). Furthermore, cell lines expressing anti-Bax $V_H$Hs showed lipid peroxidation which was statistically different from the two control treated cell (tr) (p<0.05) but similar to the ntf (ntr) cells (p>0.05).

Figure 12:
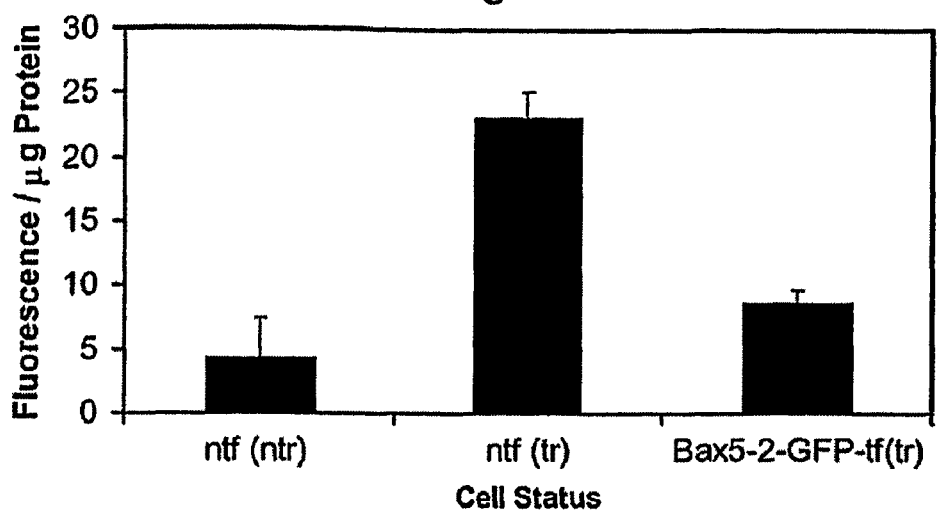

FIG. 12. Caspase 3/7 activation was prevented by anti-Bax intrabodies. A high throughput screening assay was used to quantify the activation of Caspase 3/7 in non-transfected (ntf) control (non-treated, ntr, or treated, tr) cells as well as those expressing Bax5-2 $V_H$Hs. A fluorescence plate reader was used to detect the fluorescence produced due to high levels of active caspases. Oxidative stress was induced using 100 μM $H_2O_2$ for 1 h and readings were taken after 6 h. Cells expressing Bax5-2 $V_H$H produced low levels of fluorescence comparable to control cell line without any treatment (ntf (ntr)), indicating a decrease in caspase activation due to protection of mitochodria by the anti-Bax intrabody. In contrast, non-transfected, treated cells (ntf (tr)) produced significantly high levels of fluorescence, with p values less than 0.05 when compared to both ntf (ntr) and Bax5-2 expressing cells, indicating strong caspase activation in these control cell lines.

Figure 13:
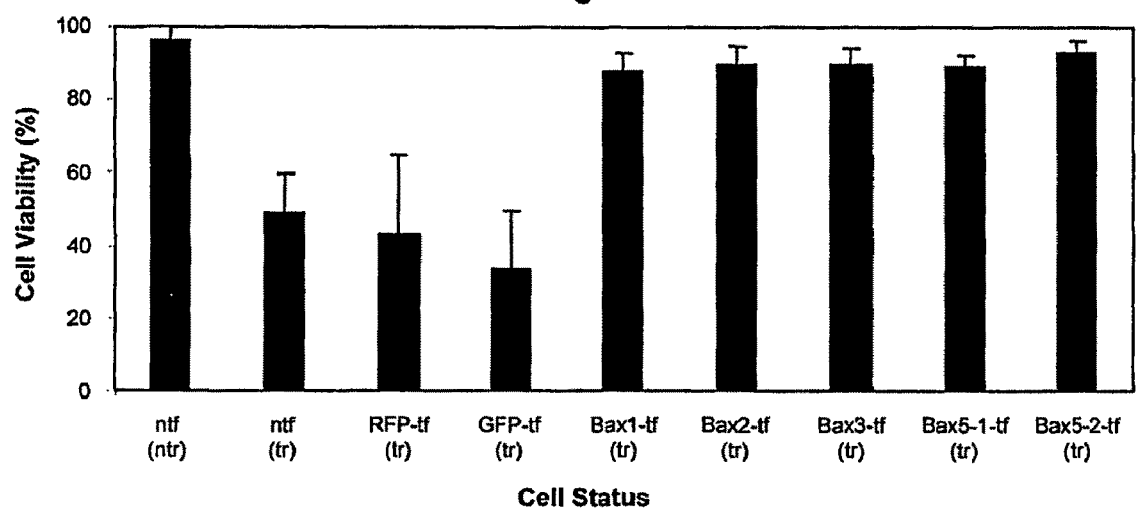

FIG. 13. Protection by $V_H$Hs against oxidative stress is not affected by the presence of the fusion fluorescent proteins.

Stable cell lines expressing $V_H$Hs (Bax1, Bax2, Bax3, Bax5-1 and Bax5-2) without the GFP/RFP fusion proteins were also established and tested for survival under oxidative stress conditions. Apoptosis was decreased in these cell lines which exhibited cell viability rates significantly higher than all the treated control cell lines (ntr, GFP-tf(tr), RFP-tf(tr), PTH50-tf(tr)), as the p values for all the anti-Bax $V_H$H expressing cells were <0.05 when compared to each of the aforementioned treated control cells.

FIG. 14. Amino acid sequences of the anti-Bax $V_H$HS. CDR1, CDR2 and CDR3 appear sequentially in bold text (SEQ ID NOS 1-6 are disclosed respectively in order of appearance). Dots represent sequence identity with Bax2 $V_H$H, and dashes are included for sequence alignment. Kabat numbering system is used (Kabat et al., 1991).

FIG. 15. Binding analysis of the anti-Bax $V_H$HS. (A) Binding of $V_H$H-displayed phages to immobilized Bax by ELISA. None of the $V_H$H-phages bound to BSA, and the phage alone showed a background binding to Bax. Definitive conclusions with respect to the relative affinity of the $V_H$Hs for Bax cannot be drawn, because the amount of $V_H$H-phage added during the binding step is not known. (B) Binding by surface plasmon resonance showing sensorgram overlays for the binding of 3.4 µM, 6.7 µM, 10 µM, 13 µM, 17 µM, 20 µM, 23 µM and 27 µM Bax2 $V_H$H to immobilized Bax.

Figure 16:
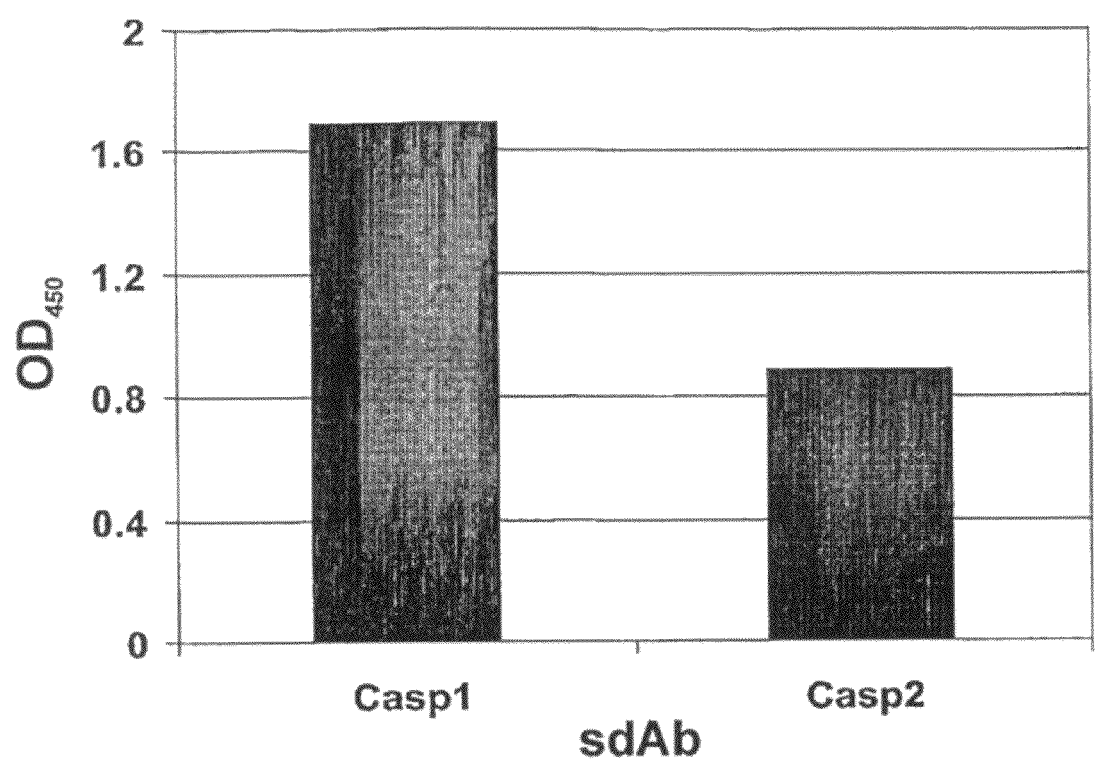

FIG. 16. Binding of anti-caspase-3$V_H$H-displayed phages to immobiized caspase-3 by ELISA. None of the $V_H$H-phages bound to BSA, and the phage alone showed a background binding to Bax.

Figures 17, 18:
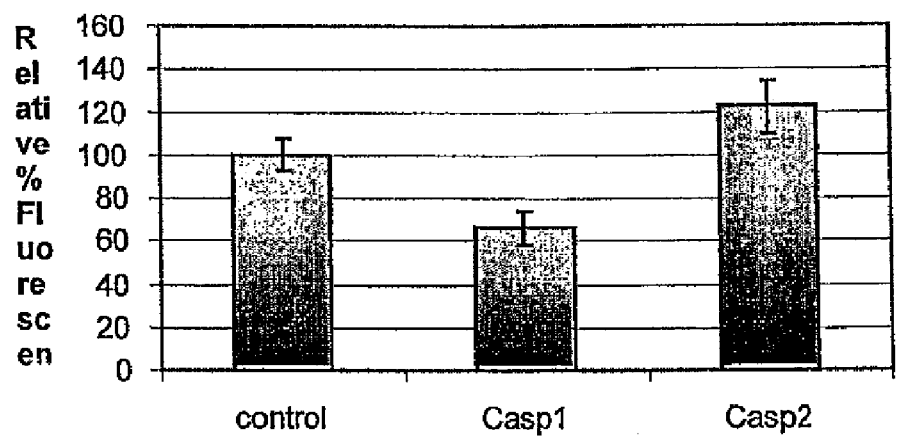

FIG. 17. Amino acid sequences of Casp1 (A) (SEQ ID NO: 7) and Casp2 (B) (SEQ ID NO: 8) $V_H$HS. CDR1, CDR2 and CDR3 appear sequentially, underlined and in bold text. CDR designations are based on Kabat numbering system (Kabat et al., 1991).

FIG. 18. Effects of Casp1 and Casp2 sdAbs on active Caspase 3 isolated from SHSY-5Y cells induced by treatment with 50 µM $H_2O_2$. Control is active caspase 3 without sdAbs added and Casp1 and Casp2 are taken as percentages relative to the control.

SUMMARY OF THE INVENTION

A first object of this invention is to identify and isolate single-domain antibodies or fragments thereof which bind to apoptotic proteins such as Bax and caspase-3.

A second object of this invention is to provide a method for modulating apoptosis or its effects through the use of single-domain antibodies which bind to apoptotic proteins such as Bax and caspase-3.

A further object of this invention is to provide a method for treating diseases or conditions, where disease symptoms are caused by undesirable cell apoptosis or oxidative stress, or where targeted cell apoptosis is desired.

There is disclosed herein the identification, cloning and functional characterization of several Bax-specific and caspase-3-specific single domain antibodies (sdAbs). These minimal size antibody fragments, which were isolated from a llama $V_H$H phage display library by panning, inhibit anti-Bax or anti-caspase-3 function in in vitro assays. Importantly, as intrabodies, these sdAbs, which were stably expressed in mammalian cells, were nontoxic to their host cells and rendered them highly resistant to oxidative-stress-induced apoptosis. These intrabodies are useful drugs on their own as well as a means for identifying small compound drugs for degenerative diseases involving oxidative-stress-induced apoptosis. The single domain antibodies and fragments may be used in the context of gene therapy or bound to amino acid sequences that allow the sdAbs to be brought into cells.

A first aspect of the invention provides for a single-domain antibody having a binding affinity for an apoptotic protein. In particular, such single-domain antibody may bind Bax or caspase-3, and such binding may inhibit or activate Bax or inhibit or promote the activation of caspase-3.

The single-domain antibody may have an amino acid sequence that comprises at least one of SEQ. ID NO.: 1, SEQ ID NO.:2, SEQ ID NO.3, SEQ ID NO.4, SEQ ID NO.5, SEQ ID NO.: 6, SEQ ID NO.: 7 and/or SEQ ID NO.: 8, or a variant or fragment thereof.

A second aspect of the invention provides for a multimer, and preferably a pentamer, comprising at least two single-domain antibodies having a binding affinity for an apoptotic protein, such as Bax or caspase-3.

A third aspect of the invention provides for a vector comprising a nucleic acid sequence encoding a single-domain antibody that binds an apoptotic protein, and a cell, preferably a human cell, that comprises the vector.

A further aspect of the invention provides for a method for modulating the symptoms of apoptosis in a cell, comprising the steps of exposing the cell to at least one single-domain antibody having a binding affinity for Bax; and allowing binding of the at least one single-domain antibody to Bax.

A further aspect of the invention provides for a method for modulating mitochondrial permeabilization in a cell, comprising the steps of exposing the cell to at least one single-domain antibody having a binding affinity for Bax; and allowing binding of the at least one single-domain antibody to Bax.

A further aspect of the invention provides for a method of modulating Bax-Bax dimerization in a cell comprising the steps of exposing the cell to at least one single-domain antibody having a binding affinity for Bax; and allowing binding of the at least one single-domain antibody to Bax.

A further aspect of the invention provides for a method for modulating the effects of oxidative stress in a cell comprising the steps of exposing the cell to at least one single-domain antibody having a binding affinity for Bax; and allowing binding of the at least one single-domain antibody to Bax.

A further aspect of the invention provides for a method for modulating the production of reactive oxygen species in a cell comprising the steps of exposing the cell to at least one single-domain antibody having a binding affinity for Bax; and allowing binding of the at least one single-domain antibody to Bax.

A further aspect of the invention provides for a method for modulating lipid peroxidation in a cell comprising the steps of exposing the cell to at least one single-domain antibody having a binding affinity for Bax; and allowing binding of the at least one single-domain antibody to Bax.

A further aspect of the invention provides for a method for modulating the release of apoptotic proteins within a cell, comprising the steps exposing the cell to at least one single-domain antibody having a binding affinity for Bax; and allowing binding of the at least one single-domain antibody to Bax.

A further aspect of the invention provides for a method for treating a disease or condition involving cell death, comprising the steps of exposing the cell to at least one single-domain antibody having a binding affinity for Bax; and allowing binding of the at least one single-domain antibody to Bax.

A further aspect of the invention provides for a method for treating a disease or condition involving cell death comprising the steps of exposing the cell to at least one single-domain antibody having a binding affinity for caspase-3; and allowing binding of the at least one single-domain antibody to caspase-3.

A further aspect of the invention provides for a method for treating cancer through induction of apoptosis in cancer cells, comprising the steps of exposing the cancer cells to at least one single-domain antibody having a binding affinity for Bax or caspase-3 and allowing binding of the at least one single-domain antibody to Bax or caspase-3.

A further aspect of the invention provides for the use of a first single-domain antibody or antibody fragment having a binding affinity for Bax or caspase-3 for identifying a second single-domain antibody or antibody fragment having a binding affinity for an apoptotic protein.

DETAILED DESCRIPTION OF THE INVENTION

The present invention relates to a variety of potential antibodies and antibody-derived fragments, including single domain fragments. As referred to herein, a single-domain fragment is a protein fragment having only one domain, the domain being preferably a variable domain derived from the immunoglobulin superfamily. It will be understood that single domain fragments may be produced by translation of all or part of a nucleic acid sequence or by other methods, including de novo chemical synthesis, and fragmentation of larger proteins, such as protease treatment of immunoglobulins. The fragment could also be an Ig superfamily variable-like domain such as the type III domain of fibronectin and the cytotoxic T lymphocyte associated antigen-4 (CTLA-4) extracellular domain.

The single-domain antibodies identified herein were obtained by screening a naïve llama $V_HH$ phage display library. Several sdAbs were isolated and characterized, and found to have binding affinities for apoptotic proteins, including Bax and caspase-3. Such binding affinities may be used to inhibit the activity of these apoptotic proteins, or alternatively to activate the proteins.

The single-domain antibodies identified include sdAbs having amino acid sequences SEQ ID NO.: 1 through SEQ ID NO.: 8 shown in the attached sequence listing. These antibody fragments were found to have apoptotic protein binding affinity. It is expected that variants or fragments of these sequences having apoptotic protein binding affinity would also be useful. The corresponding nucleic acid sequences are shown as SEQ ID NO.: 10 through SEQ ID NO.: 17. Mutants, variants, homologs or fragments of these nucleic acid sequences encoding sdAbs with apoptotic protein binding affinity will also be useful.

Single domain fragments may be modified to add additional moieties in some cases. Examples of additional moieties include polypeptides such antibody domains, marker proteins or signal proteins. Examples of antibody domains include, but are not restricted to, Immunoglubulin (Ig) light chain variable domains ($V_L$), Ig heavy chain variable domains ($V_H$), camelid (camels and llamas) heavy chain antibody variable domains ($V_HH$), nurse shark and wobbegong shark Ig new antigen receptor (IgNAR) variable domains ($V_H$), T cells receptor variable domains. Examples of marker proteins include red or green fluorescent protein, or radioisotopes. Examples of signal proteins included mitochondrial or nuclear transport signal proteins. Another possibility is the addition of leader sequences to the nucleic acid sequences encoding the sdAbs—these could determine cellular localization of the sdAbs.

The single-domain antibodies or fragments of the present invention may be incorporated into viral or plasmid vectors. These vectors can then be incorporated into cells, including human cells.

The non-toxic, Bax-specific and caspase-3-specific $V_HH$ intrabodies of the present invention phenotypically transform their host neuronal cells into cells which are resistant to oxidative-stress-induced apoptosis. This opens new opportunities for treating neurodegenerative diseases which involve cell death induced by oxidative stress and Bax activation. In particular, the sdAbs and fragments of the present invention may be used to modulate the symptoms of cell apoptosis. Exposure of these sdAbs and fragments to cells (typically by the expression of the sdAbs within the cells) can promote or prevent apoptosis through binding of the sdAbs with apoptotic proteins such as Bax and caspase-3. For example, binding of sdAbs to Bax can prevent or promote mitochondrial permeabilization, as Bax is thought to play a significant role in this process. Thus, the inhibition of Bax can prevent mitochondrial permeabilization, while the activation of Bax can promote this process. Closely related to mitochondrial permeabilization is the release of apoptotic proteins such as cytochrome c, apoptosis inducing factor, and caspase-9, and accordingly Bax-binding sdAbs may be used to modulate the release of apoptotic proteins.

Other examples of uses for Bax-binding sdAbs include modulating the effects of oxidative stress in cells, modulating the production of reactive oxygen species in cells, and modulating lipid peroxidation in cells. Oxidative stress may lead to cell apoptosis, and accordingly the use of Bax or caspase-3 binding sdAbs to promote or prevent apoptosis allows for modulation of the effects of oxidative stress. The production of reactive oxygen species and the peroxidation of cell lipids are examples of effects caused by oxidative stress in the cell, and accordingly these can be modulated through the use of sdAbs with binding affinities for apoptotic proteins.

Similarly, the sdAbs of the present invention may be used to promote or prevent the dimerization of Bax. Where, for example, sdAbs bind to Bax at its dimerization site or in such a way that Bax dimerization is not possible, the apoptotic processes initiated by the activated Bax dimer cannot take place. By contrast, where sdAbs bind to Bax at a site that does not block Bax-Bax dimerization, this dimerization may be promoted by, for example, the use of multimerized sdAbs as discussed below.

Several research groups are working towards utilizing intrabodies as therapeutic agents in various diseases (Miller, T. W. et al., 2005). Other than the direct use of these intrabodies, these sdAbs could be used as biochemical tools to fish out specific and non-toxic inhibitors of Bax from pharmacophore libraries. Furthermore, fluorescence or radio-labeled anti-Bax sdAbs and the oxidative-stress resistant cell lines would be a valuable research tools to elucidate the mechanism of mitochondrial permeabilization and apoptosis in general.

The current anti-Bax $V_HHs$ and single domain fragments can be used in the diagnosis and therapy of several diseases, especially those involving cell death, including neurodegenerative diseases, cardiovascular diseases, stroke, AIDS and cancer.

Anti-caspase fragments can be used in the treatment and amelioration of a variety of diseases and disorders, either to induce or to inhibit apoptosis. For example, anti-caspase single domain fragments capable of inhibiting caspase-3 activity or inhibiting activation of caspase-3 can be used in blocking cell death in Alzheimer's disease, Parkinson's disease, AIDS and stroke. Conversely, anti-caspase or anti-Bax single domain fragments capable of activating caspase-3 may also be used as anticancer agents to induce apoptosis in cancer cells.

Delivery of the anti-caspase and anti-Bax antibodies and antibody fragments to cells may be accomplished by various methods. In the context of gene therapy, nucleic acid sequences encoding the antibodies may be delivered into cells as viral vectors, such as adenovirus, vaccinia virus or adeno-associated virus. For example, a protein such as an antibody or antibody fragment having specificity for a particular cell surface molecule may be attached to the surface of the virus, allowing the virus to target specific cells. Further, the virus may be engineered to contain nucleic acid sequences, such as promoters, which allow the virus to function in only particular cells, such as cancer cells.

Another option is the delivery of single-domain antibodies in the form of immunoliposomes. Such liposomes may contain single-domain antibodies or fragments (as genes or as proteins), and may be designed to specifically target the DNA-lipid complex of the target cells.

Single-domain antibodies may also be delivered to cells such as cancer cells in nucleic acid form through a bifunctional protein. For example, the bifunctional protein may include both an antibody specific to a cancer cell and a nucleic acid binding protein such as human protamine. The binding protein would attach to the sdAb gene and the antibody would allow specific cells to be targeted.

Alternatively, treatment for these diseases may be accomplished through delivery to cells in a protein form. This may be accomplished by fusing the sdAb to a membrane translocating sequence (MTS) or protein transduction domain (PTD) to allow for transportation across the plasma membrane. Another option is to fuse the sdAb to an internalizing protein (eg. internatlizing antibody or antibody fragment) which allows the sdAb to be internalized by the cell.

In cases where it is desirable for the single-domain antibodies to cross the blood-brain barrier, the sdAb may be fused to a polypeptide capable of crossing this barrier, or the nucleic acid sequence encoding the sdAb may be part of a viral vector which is capable of crossing the barrier. Additional means (as discussed above) for delivering the sdAb to brain cells once it has crossed the blood-brain barrier would still be required.

In a therapeutic setting, the $V_H$Hs can also exert their effect by modulating the action of Bax by functioning as shuttles, taking Bax to desired cell compartments, e.g., nucleus. This is done by attaching specific signal sequences to $V_H$Hs through genetic engineering or molecular biology techniques.

In some instances it will be desirable to use conjugates or fusion proteins comprising single domain binders and a domain allowing homo or hetero-multimerization. In particular, as discussed below, the formation of multimers, and in particular pentamers, of single domain intrabodies may increase the binding affinity of the sdAbs.

One possible application of a multimerized sdAb would be that more than one bound apoptotic protein could be brought together. This may be useful in the case of apoptotic proteins such as Bax and caspase-3 which dimerize or multimerize in order to take an active form through, for example, cleaving of sulphide bonds as in the case of caspase-3. Accordingly, if two or more inactive caspase-3 molecules are brought together by a sdAb pentamer or other multimer, they can cleave each other and thus be activated.

Identification of Anti-Bax $V_H$Hs

Figure 15A:
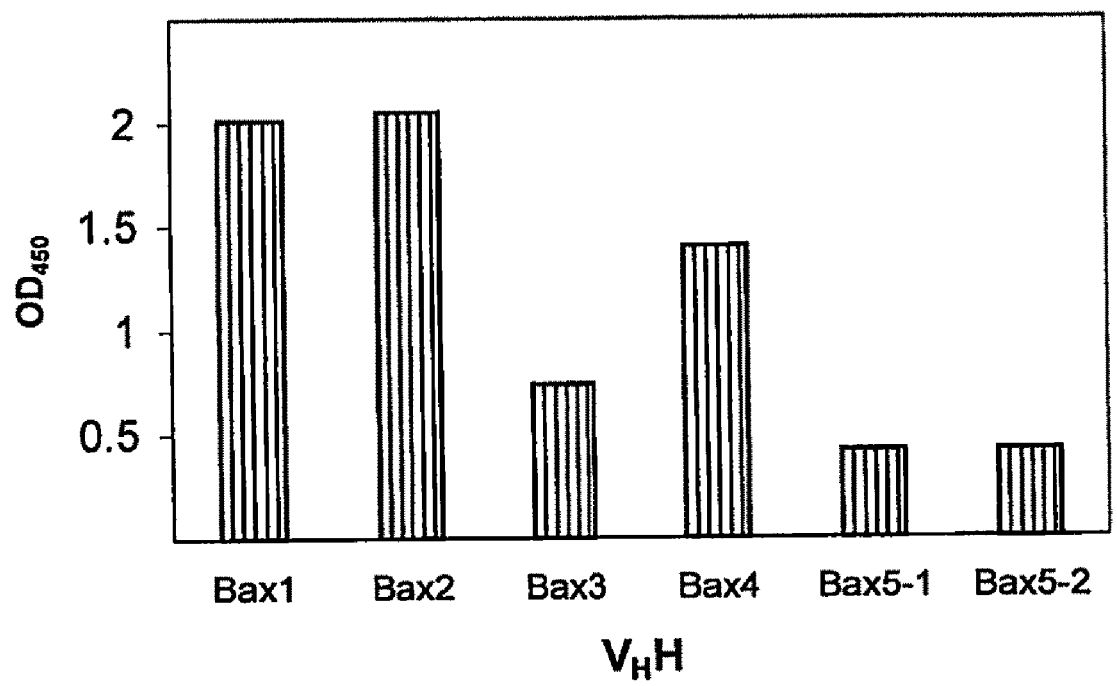
Figure 15B:
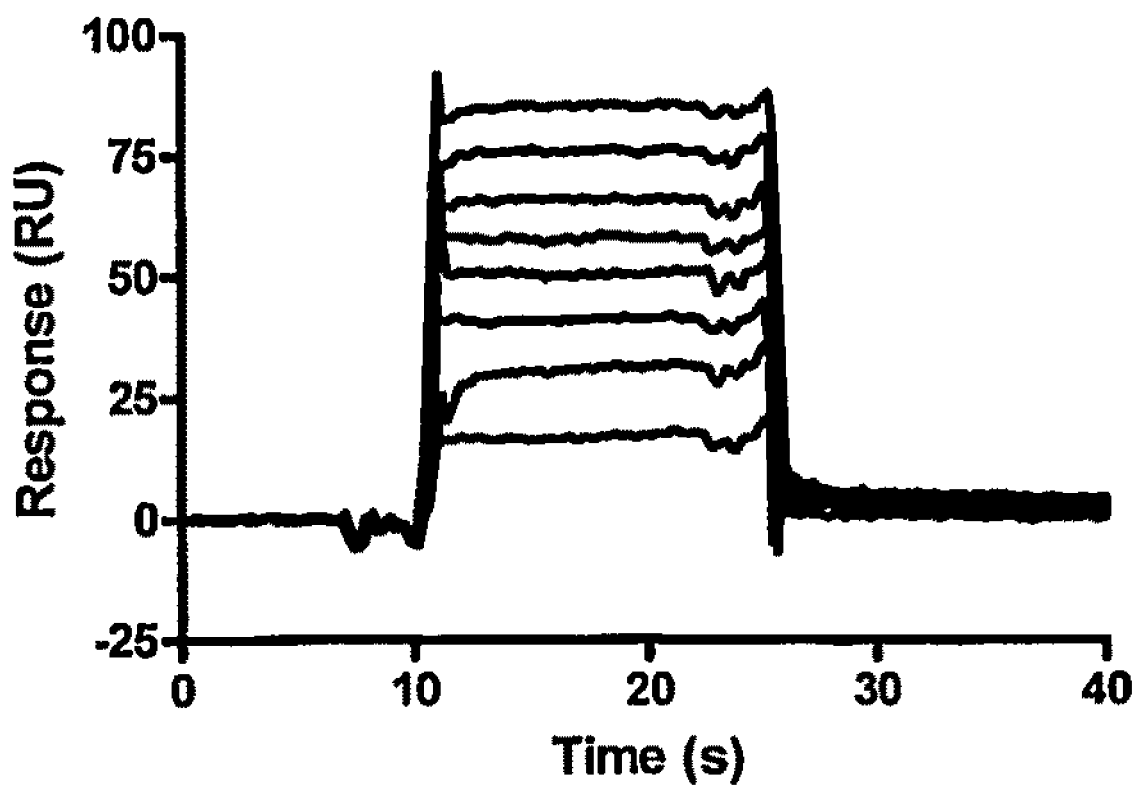

Anti-apoptotic single-domain intrabodies were Identified by screening a naïve llama $V_H$H phage display library (Tanha, J. et al., 2002e) against Bax. Screening of 38 colonies from the second and the third rounds of panning gave six different $V_H$H sequences, namely, Bax1, Bax2, Bax3, Bax4, Bax5-1 and Bax5-2, occurring at frequencies of 9, 24, 2, 1, 1 and 1, respectively (FIG. 14). All six $V_H$Hs bound strongly to Bax but not to control BSA antigen in phage ELISAs (FIG. 15A). $V_H$Hs were expressed as fusion protein with C C-terminal c-Myc-His$_5$ tag (SEQ ID NO: 9) in $E.$ $coli$ and purified to homogeneity for subsequent functional studies. Bax2 was chosen to provide an example for confirming the ELISA binding data by surface plasmon resonance (SPR) because of its availability at desirable quantities. The $V_H$H was specific to Bax, as it did not bind to a control Fab, with equilibrium dissociation constant ($K_D$) of 40 µM (FIG. 15B). Binders obtained previously from the naïve $V_H$H phage display library (Tanha, J. et al., 2002d) have had $K_D$S in the low micromolar range with $K_D$s of a few micromolar at best (Yau, K. Y. et al., 2003; Yau, K. Y. et al., 2005).

Functional Characterization of $V_H$Hs In Vitro: Inhibition of Bax Activity in Isolated Mitochondria The ability of the six $V_H$Hs to inhibit Bax was tested by monitoring Bax-induced ROS generation from isolated mitochondria, which as mentioned above correlates with mitochondrial destabilization (Nomura, K. et al., 2000). We hypothesized that if the anti-Bax $V_H$Hs are inhibitory towards Bax, pre-incubation of isolated mitochondria with anti-Bax $V_H$HS, followed by the addition of Bax should prevent Bax from permealizing the mitochondria and lead to a reduced ROS release from mitochondria into the solution. Indeed, for all the $V_H$Hs (Bax1, Bax2, Bax3, Bax4, Bax5-1 and Bax5-2) tested, we observed a significant decrease in ROS release from mitochondria incubated with $V_H$Hs and Bax compared to the fractions of mitochondria incubated with Bax alone or with Bax and an irrelevant $V_H$H ($p<0.05$) (FIG. 2A).

Specifically, Bax3 and Bax5-2 $V_H$Hs showed greatest potential as Bax inhibitors decreasing ROS production from mitochondria by approximately 55% and 90%, respectively. $V_H$Hs can inhibit the Bax function by binding to Bax at several sites: on the Bid-binding site, on the transmembrane domain and/or at the site involved in Bax-Bax dimerization and activation. The variability of inhibition by different sdAbs suggests that these sdAbs might be blocking different sites on Bax. Specifically, Bax5-2 is likely binding a site involved in Bax function as it has the maximum inhibitory effect.

Permeability of the mitochondria was also monitored through detection of cytochrome c release by Western blot. Cytochrome c is released from the inner mitochondrial space into the solution when this organelle is destabilized (Adhihetty, P. J. et al., 2003). Thus, stable and healthy mitochondria are expected to show strong retention of cytochrome c. As in the previous ROS assay, isolated mitochondria in solution were pre-incubated with $V_H$Hs followed by the addition of Bax (mitochondria alone and in presence of recombinant Bax protein only were used as controls). When incubated with Bax, significantly higher cytochrome c release was seen in the supernatant fraction of the mitochondria incubated with recombinant Bax protein alone compared to those incubated with $V_H$Hs and Bax (FIG. 2B), these findings were further confirmed by calculating the percent integrated density value of each band intensity (FIG. 2C). Equal protein sample loading was confirmed in both instances by Ponseau S staining of the blots before incubation with blocking solution (data not shown). Conversely, mitochondria preincubated with $V_H$Hs showed significantly more cytochrome c in its pellet fraction (representing intact mitochondrial membrane) than the ones with no preincubation, demonstrating that the $V_H$Hs decreased the permeability of mitochondria initiated by Bax (data not shown).

Figure 3B:
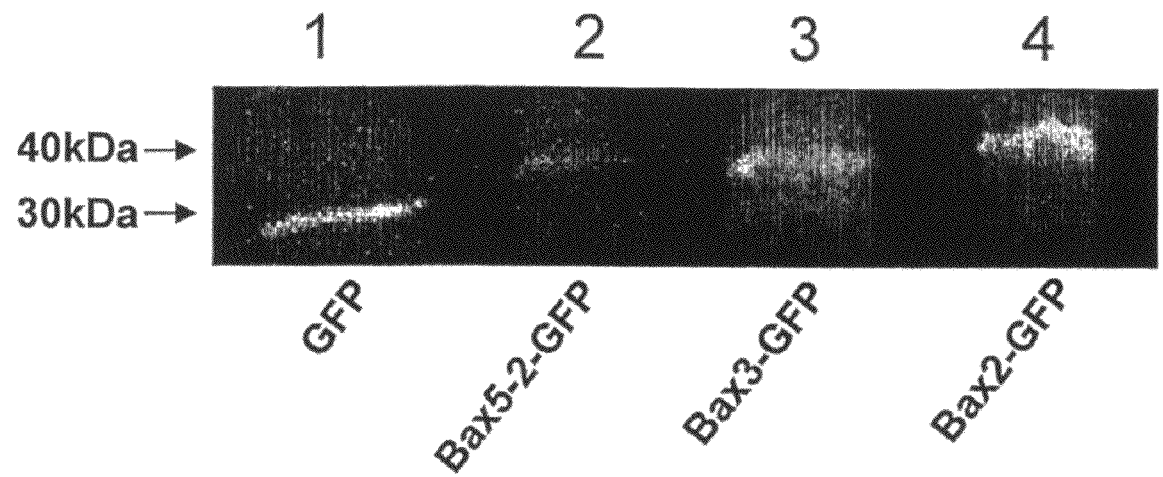
Figure 3C:
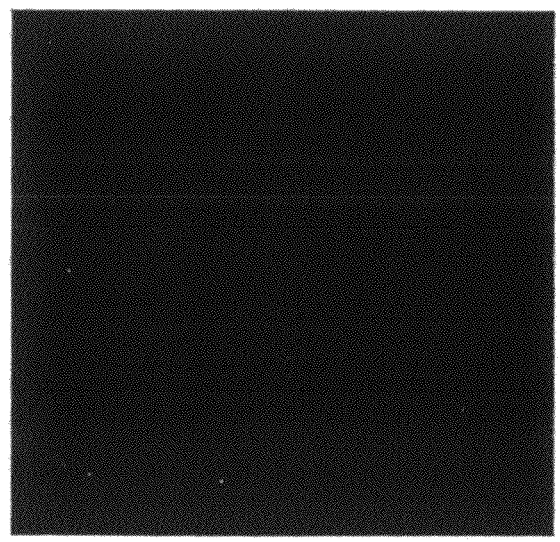

Functional Characterization of Anti-Bax $V_HH$s In-Situ: Inhibition of Apoptosis by $V_HH$s when Expressed as Intrabodies in Mammalian Cells The assays performed on isolated mitochondria clearly indicated that the $V_HH$s can bind and prevent Bax activity in solution and in isolated mitochondria. We further studied the effects of the $V_HH$s as intrabodies inside intact cells. SHSY-5Y cells were transfected with all six $V_HH$ genes in fusion with RFP and GFP (FIG. 3A) and 12 stable cell lines, each expressing a unique $V_HH$ fusion protein, were obtained. In addition, stable control cell lines containing genes for an irrelevant $V_HH$ (PTH50, a parathyroid-hormone binding $V_HH$) or fluorescent proteins alone were established. Expression of the $V_HH$s from both transient and stable transfections was confirmed by Western blot analysis of cell lysates using anti-GFP antibody (FIG. 3B). In lane 1, cells containing GFP produce a band just under 30 kDa, consistent with the GFP molecular weight, 27 kDa (Battistutta, R. et al., 2000), while cells expressing each of, the six anti-Bax $V_HH$-GFP fusion proteins produce a band at approximately 40 kDa, very close to the theoretical value, 41 kDa (Bax5-2, Bax3 and Bax2 are shown). Fluorescence microscopy was also used to "visualize" expression of $V_HH$-RFP or $V_HH$-GFP fusion proteins in cells (FIG. 3C, Bax4-RFP is shown).

To assess the protective capabilities of the six Bax-specific $V_HH$s in context of intrabodies, we again monitored the resistance of cells to apoptosis under oxidative stress. As previously discussed, oxidative stress due to mitochondrial ROS elevation, has been linked to the activation of Bax and ultimate destabilization of the mitochondria leading to apoptosis (Susin, S. A. et al., 1999; Adhihetty, P. J. et al., 2003). Thus, we hypothesized that if the $V_HH$ intrabodies block Bax activity during oxidative stress, apoptosis would be prevented. In previous studies it was shown that exposure of SHSY-5Y cells to 100 μM $H_2O_2$ for 1 h results in a significant increase in the rate of apoptosis (Somayajulu, M. et al., 2005). By implementing this condition to the stable cell lines containing either a $V_HH$ gene or a control gene we monitored the cells 24 h after $H_2O_2$ treatment for apoptotic features. To this end, the cells were stained with Hoechst reagent where brightly stained and condensing nuclei would be indicative of apoptotic cells (FIG. 4).

Untreated SHSY-5Y cells not expressing any $V_HH$ were used as a positive control with approximately 96% cell viability (FIG. 5). When the three negative control cell lines (non-transfected, transfected with GFP or RFP only or transfected with PTH50) were exposed to 100 μM $H_2O_2$, a significant number of cells underwent apoptosis 24 h after the treatment as indicated by brightly stained condensed nuclei. Thus, the number of non-apoptotic healthy cells was reduced to approximately 50% (FIG. 5). Interestingly, the cells containing any of the six anti-Bax $V_HH$ intrabodies in fusion with GFP or RFP showed very good resistance to the similar treatment with 87-93% viabilities and varied significantly from all the control treated cell lines (p<0.05). These values are very close to the viability values for the untreated, non-transfected SHSY-5Y cells (96%), demonstrating the effectiveness of the $V_HH$ intrabodies in preventing apoptosis.

Annexin V in parallel with Hoechst staining (FIG. 6) was used to monitor plasma membrane flipping (another indicator of the early phase of apoptosis) and nuclear condensation respectively. These assays further confirmed the above finding that apoptosis was inhibited in the cells expressing anti-Bax $V_HH$S. Moreover, the expression of $V_HH$s was non-toxic to their host cells as growth and proliferation was not hindered. The $V_HH$-containing cells that survived the oxidative stress were viable and fully functional after several days following $H_2O_2$ treatment (FIG. 7) as their growth rate was similar to those without any oxidative stress.

Intrabodies Prevent Mitochondrial Membrane Potential Collapse Following Oxidative Stress and Render the Host Cells Resistance to Apoptosis at Higher Level of Oxidative Stress To further assess the degree of potency of the $V_HH$ intrabodies in preventing apoptosis, we increased the stress conditions. When the $H_2O_2$ (100 μM) exposure time was increased to 3 h, cells expressing $V_HH$s showed almost identical survival rates as when exposed for 1 h (data not shown). When treated with 200 μM $H_2O_2$ for 1 h, control cell lines (containing no or the irrelevant $V_HH$) showed a very high degree of apoptosis and poor survival as measured by Hoechst staining and trypan blue exclusion assay. Conversely, almost all cell lines contain each of the $V_HH$s showed significant survival, with the most promising being the cells containing Bax1, Bax2, Bax3, Bax4, Bax5-1 and Bax5-2 $V_HH$s (FIG. 8). As before, the cell viabilities of the anti-Bax $V_HH$ expressing cells were shown to be statistically higher than all the control treated cell lines (p<0.05). Importantly, these results are in agreement to the ROS data (FIG. 2A) obtained using $V_HH$s in presence of isolated mitochondria. In addition, JC-1 staining of mitochondrial membrane potential after the 200 μM $H_2O_2$/1 h treatment (FIG. 9) showed stable mitochondrial potential in cells expressing the anti-Bax $V_HH$s comparable to the non-transfected, non-treated control SHSY-5Y. These results were further quantified using a newly developed mitochondrial membrane potential assay called MitoCasp assay. In this assay, a cell permeable cationic dye when exposed to cell fractions is accumulated in healthy mitochondria and exhibits a strong fluorescence signal (in the red), which can be measured using a fluorescence plate reader. Collapse of mitochondrial membrane potential leads to a decrease in the fluorescence. Results shown in FIG. 10 indicated that there was a considerable decrease in the fluorescence in the non-transfected SHSY-5Y cells after 100 μM $H_2O_2$/1 h treatment, compared to the non-treated control cells and the treated Bax5-2 expressing cells (p<0.05). Conversely, cells expressing Bax5-2 $V_HH$ produced strong fluorescence comparable to control non-transfected/non-treated SHSY-5Y cell (p>0.05). This data further confirms the ability of these intrabodies to protect the mitochondria from Bax-mediated permealization in the presence of oxidative stress (FIG. 10).

In addition, we also monitored lipid peroxidation, another indicator of oxidative stress. When cells are exposed to higher ROS levels, most commonly due to mitochondrial damage, lipid deterioration is observed (Sunderman, F. W., Jr. et al., 1985). Lipid peroxidation was assessed for cells expressing anti-Bax $V_HH$s as well as non-transfected cells (with and without treatment), 24 h after exposure to 100 μM $H_2O_2$ for 1 h. We observed a significant decrease in lipid peroxidation in cells expressing anti-Bax $V_HH$S, compared to non-transfected/treated SHSY-5Y cells (FIG. 11; Bax3 and Bax5-2 are shown) (p<0.05). This indicates that the $V_HH$s are able to block mitochondrial permeabilization by Bax, thus, limiting the leakage of various apoptotic inducing factors and ultimately preventing cell death.

Activation of executioner caspases 3/7 was also monitored in $V_HH$ transfected cells using a high throughput screen for Caspase 3/7 assay kit measuring the activity of these proteases as an increase in fluorescence. Specifically, this kit utilized a quenched (z-DEVD)$_2$-R110 peptide which is cleaved by active caspases 3/7 to release R110 free dye from the quenching caspase substrate DEVD. In this way the increase in fluorescence is indicative of caspase 3/7 activation in vivo. For this assay, oxidative stress was induced in control non-transfected (non-treated or treated) cells and Bax5-2 $V_HH$-expressing cells (100 μM $H_2O_2$/1 h) and caspase activation was measured after 6 h. We observed a significant increase in fluorescence indicative of strong caspase activation in control non-transfected/treated SHSY-5Y cells which was significantly lower in non-transfected/non-treated and Bax5-2 expressing cells (p<0.05) (FIG. 12).

Presence of GFP or RFP as Fusion Proteins does not Alter the Anti-Apoptotic Activities of Anti-Bax Intrabodies To further show that anti-apoptotic activities of the anti-Bax $V_HH$s are independent of their fusion context, cell lines of $V_HH$ intrabodies without fusion to GFP or RFP were also established. These cells were also monitored for their ability to resist oxidative stress induced apoptosis by treatment with 200 μM $H_2O_2$ for 1 h. Apoptosis was monitored after 24 h using Hoechst staining to detect apoptotic nuclei. As shown in FIG. 13, cells expressing the "un-fused" anti-Bax $V_HH$s have cell viability rates which were significantly higher than all the treated control cell lines (p<0.05), indicating that the cells transfected without the fluorescent marker protein have comparable cell survival rates to their respective cells with fused $V_HH$. These results clearly indicate that inhibition of apoptosis was solely due the $V_HH$s and not due to the marker fusion protein.

Screening of Phage Display Library and Identification of Anti-Caspase-3 sdAbs.

A naïve llama $V_HH$ phage display library was screened against caspase-3. Following three rounds of panning, 41/92 sdAbs clones screened by phage ELISA were positive for binding to caspase-3. Twenty four of these were sequenced, giving two different sdAb sequences, namely, Casp1 and Casp2, occurring at frequencies of 22 and 2, respectively (FIG. 17). As shown in FIG. 16, both sdAbs are specific to caspase-3 and do not bind to a control antigen. Both sdAbs were subcloned as fusion proteins with C-terminal c-Myc-$His_5$ tag (SEQ ID NO: 9), expressed in E. coli and purified to homogeneity for subsequent functional studies. Additionally, both sdAbs were cloned into mammalian expression vectors pEGFP-N1 and pDsRed-N1 for in vivo intrabody functional studies.

Increasing the Efficacy of sdAb Intrabodies by Converting them to Pentabodies

In addition to stability and expression level, the efficacy of intrabodies is also determined by affinity. Since the active forms of Bax and caspase-3 are multimers, their binding to sdAbs can be increased by multimerizing their sdAb binding partners (i.e., increasing affinity through avidity increase). Converting sdAb monomers to pentabodies has been shown to increase their apparent affinity by several thousand fold-fold without compromising their expression yields and stability (Zhang, J. et al., 2004a).

All six anti-Bax $V_HH$s (FIG. 1) were pentamerized substantially by the method of (Zhang, J. et al., 2004b) as described. All were shown to have acquired drastic increase in binding affinity by surface plasmon resonance as shown previously (Zhang, J. et al., 2004c).

Panning and phage ELISA. A llama $V_HH$ phage display library described previously was used in panning experiments (Tanha, J. et al., 2002c). Panning against recombinant Bax and caspase-3 proteins was performed as described (Tanha, J. et al., 2002b) except that, in the case of Bax in the second and the third rounds, the phage elution additionally involved $MgCl_2$/HCl treatment. First, the bound phages in the microtiter wells were eluted with 200 μl TEA and neutralized with 100 μl 1 M Tris-HCl pH 7.4 (Tanha, J. et al., 2002a). Then, the emptied wells were subsequently incubated with 100 μl of 4 M $MgCl_2$ at room temperature for 15 min. The eluted phage was removed and the wells were incubated with 100 μl of 100 mM HCl for five min at room temperature. The $MgCl_2$/HCl-eluted phages were pooled, neutralized with 1.5 ml of 1 M Tris-HCl pH 7.4 and combined with the TEA-eluted phages. One ml of the combined phages was used to infect E. coli for overnight phage amplification and the remaining 1 ml was stored at −80° C. for future reference. $V_HH$ clones were identified from the titer plates by plaque PCR and sequencing as described (Tanha, J. et al., 2003). Following panning, phage clones from titer plates were amplified in microtiter wells (Tanha, J. et al., 2003) and screened for binding to Bax protein by standard ELISA procedures using a HRP/anti-M13 monoclonal antibody conjugate (Amersham Biosciences, Baie d'Urfe, QC, Canada) as the detection reagent.

Protein expression and purification. $V_HH$s were cloned from the phage vector into the expression vectors by standard cloning techniques (Sambrook, J. Fritsch E. F. and Maniatis T, 1989). E. coli expression of $V_HH$s and subsequent purification by immobilized metal affinity chromatography were performed as described (Tanha, J. et al., 2003). Protein concentrations were determined by $A_{280}$ measurements using molar absorption coefficients calculated for each protein (Pace, C. N. et al., 1995). Mammalian expression of $V_HH$ fusion constructs was initiated by inserting the $V_HH$ genes in the Hind III/BamH I sites of pEGFP-N1 ($V_HH$-GFP fusion) or pDsRed1-N1 ($V_HH$-RFP fusion) (BD Biosciences, Mississauga, ON, Canada) (FIG. 3A). The $V_HH$ recombinant vectors were subsequently used to transfect human neuroblastoma cells (SHSY-5Y) as described below.

$V_HH$ pentabody constructions. Pentabody cloning, expression, purification and binding analysis by surface plasmon resonance were carried out as described (Zhang, J. et al., 2004d)

Surface plasmon resonance. Equilibrium dissociation constant, $K_D$, for the binding of Bax2 $V_HH$ to Bax was derived from SPR data collected with BIACORE 3000 biosensor system (Biacore Inc., Piscataway, N.J.). To measure the binding, 1800 RUs of protein Bax or 1100 RUs of a reference Fab were Immobilized on research grade CM5 sensor chips (Biacore Inc.). Immobilizations were carried out at concentrations of 12 μg/ml (Bax) in pH 4.0 or 25 μg/ml (Fab) in pH 4.5, 10 mM sodium acetate buffer, using the amine coupling kit provided by the manufacturer. Analyses were carried out at 25° C. in 10 mM HEPES, pH 7.4, containing 150 mM NaCl, 3 mM EDTA and 0.005% P20 surfactant at a flow rate of 40 μl/min, and surfaces were regenerated by washing with the running buffer. Data were fit to a 1:1 Interaction model simultaneously using BIAevaluation 4.1 software (Biacore Inc.) and $K_D$ was subsequently determined.

Cell culture. Human neuroblastoma (SHSY-5Y) cells (ATCC, Manassas, Va.) were grown in complete medium consisting of DMEM Ham's F12 media (Invitrogen Canada Inc., Burlington, ON, Canada) with the addition of 2 mM L-glutamine (Invitrogen Canada Inc.) and 10% (v/v) fetal bovine serum (Sigma, Oakville, ON, Canada) and 20 μg/ml gentamycin (Invitrogen Canada Inc.). 200 μg/ml Geneticin (G418) (Invitrogen Canada Inc.) was added to all transfected cells. The cells were incubated at 37° C. with 5% $CO_2$ and 95% humidity.

Statistical analysis. p values for all graphs were calculated using Statistica Application for Windows 95, where p values less than 0.05 were assumed to be statistically different.

$V_HH$ isolation and mitochondria ROS measurement. SHSY-5Y cells were grown to 70% confluence in 10-ml Petri dishes. The intact mitochondria were isolated from these cells using a previously published method (Li, N. et al., 2003a). Mitochondria were suspended in solution containing 0.25 M sucrose, 1 mM $MgCl_2$, 10 mM HEPES, 4 mg/ml p-hydroxyphenyl acetic acid (PHPA) and 20 mM succinate (Sigma Canada). Mitochondrial ROS generation is measured by $H_2O_2$ generation rate, determined fluorimetrically by measurement of the oxidation of PHPA coupled to the reduction of $H_2O_2$ by horseradish peroxidase (Sigma Canada), based on a previously published protocol (Li, N. et al., 2003b).

Detection of cytochrome c release by Western blot. Cytochrome c release was detected after incubating isolated mitochondria with $V_HH$ for 15 min followed by exposure to Bax for 5 min, in solution containing 0.25 M sucrose, 1 mM $MgCl_2$, 10 mM HEPES, and 20 mM succinate. Samples were then spun down at 10,000 g for 5 min separating proteins of whole intact mitochondrial (pellet) and those released due to mitochondrial membrane permealization (supernatant). Pellet and supernatant fractions were solubilized in SDS-PAGE (sodium dodecyl sulfate-polyacrylamide gel electrophoresis) loading buffer and proteins (50 mg protein/well) were then subjected to a 12% SDS-PAGE, followed by transfer on nitrocellulose membrane. The blots were probed with monoclonal anti-cytochrome c antibodies (Santa Cruz Biotechnology Inc, Santa Cruz, Calif.) followed by washing and a second incubation with horse radish peroxidase-conjugated anti-mouse antibodies. The blots were developed using a ChemiGlow West kit (Alpha Innotech Corporation, San Leonardo, Calif.) and recorded using an Alpha Innotech Corporation Imaging System. Integrated density values were calculated using ChemImanager V5.5 program for Windows 95.

Mammalian cell transfection. Mammalian transfection of $V_HH$ fusion constructs was initiated by inserting the $V_HH$ genes in the Hind III/BamH I sites of pEGFP-N1 ($V_HH$-green fluorescent protein (GFP) fusion), pDsRed1-N1 ($V_HH$-red fluorescent protein (RFP) fusion) or Hind III/Not I site of pEGFP-N1 ($V_HH$) (BD Biosciences, Mississauga, ON, Canada). The $V_HH$ recombinant vectors were propagated in *E. coli* and were purified using QIAprep® Spin Miniprep kit according to the manufacture's instructions (QIAGEN, Mississauga, ON, Canada). The purified plasmids were subsequently used to transfect SHSY-5Y cells using Fugene 6 Transfection Reagent (Hoffmann-La Roche Ltd., Mississauga, ON, Canada) following manufacturer's protocol. Forty eight hours after transfection, cells were transferred to complete DMEM media (as described above) containing 300 µg/ml Geneticin for selection of positive transfected cells for 1-2 weeks. Stable cell lines were subsequently maintained in complete DMEM media as described above with 200 µg/ml Geneticin.

Detection of $V_HH$ expression in mammalian cells by Western blot. Equal amounts of protein extract (50 µg) from control cells containing GFP only and cells expressing specific GFP linked anti-Bax $V_HH$s were resolved by SDS-PAGE and transferred to a nitrocellulose membrane. The blots were probed with monoclonal anti-GFP antibodies (Sigma, Saint Louis, Mo.) after which they were washed and incubated with horse radish peroxidase-conjugated anti-mouse antibodies. The blots were developed as described above.

Induction of oxidative stress. Working solutions of $H_2O_2$ was made by diluting a 10 M stock of $H_2O_2$ solution with distilled water to a concentration of 100 mM. SHSY-5Y cells were grown to approximately 70% confluence. Oxidative stress was induced by incubating the cells in complete media containing either 100 µM or 200 µM $H_2O_2$ for 1 h or 3 h at 37° C. The media was then replaced with fresh, complete media (without $H_2O_2$) and the cells were incubated for different time periods to monitor apoptotic features and oxidative stress parameters.

Monitoring nuclear morphology. Nuclear morphology was monitored as an indicator for apoptosis in cells by staining cells with Hoechst 33342 (Invitrogen Canada Inc.) to a final concentration of 10 µM. After incubating for 10 min at 37° C., the cells were then examined under a fluorescence microscope (Zeiss Axioskope 2 Mot plus, Gottingen, Germany) and fluorescence pictures were taken using a camera (QImaging, Gottingen, Germany). The images were processed using Improvision OpenLab v3.1.2, Jasc Paint Shop Pro v8.00 and Adobe Photoshop v8.0.

Mitochondrial membrane potential detection and measurement. Mitochondrial membrane potential was detected using JC-1 mitochondrial specific dye (Invitrogen Canada Inc.). The cells were treated with 10 µM JC-1 and incubated for 40 min at 37° C. The cells were observed under the fluorescent microscope and fluorescence pictures were taken and processed as described above. Alternatively, mitochondrial membrane potential stability was also quantified using Dual Sensor: MitoCasp™ Assay (Cell Technology Inc, Mountain View, Calif.) as per manufacturer's instructions.

Monitoring plasma membrane flipping. Annexin V (Invitrogen Canada Inc.) was used to monitor plasma membrane flipping in cells according to manufacturer instructions. After incubating for 15 min at 37° C., the cells were examined under the fluorescence microscope and fluorescence pictures were taken and processed as described above.

Lipid peroxidation determination. Lipid peroxidation in cells was determined using the thiobarbituric acid-reactive substances (TBARS) reaction with malondialdehyde and related compounds as previously described (Sunderman, F. W. Jr Takeyama N. et al., 1985-52002).

Caspase 3/7 activation measurement. The activation of Caspase 3/7 was measured in cells using Apo 3/7 HTS™ High Throughput Screen Assay kit (Cell Technology Inc, Mountain View, Calif.) as per manufacturer's instructions.

Activation of Caspase 3 Via Induction of Oxidative Stress

Plated SHSY-5Y cells of approximately 70% confluency were treated with 100 µM H2O2 (1 µL per mL of media) for 1 hour to produce reactive oxygen species (ROS). The ROS In turn cause permeability of the mitochondria, leaking cytochrome c and initiating the Caspase cascade, leading to the activation of Caspase 3. After 1 hour the media was removed and replaced with new media and the cells were incubated for 3 hours. Following the incubation, the plates were trypsinized (0.15% trypsin) to remove the cells from the plate and the samples were collected in tubes. The tubes were centrifuged at 35000 rpm for 7 minutes at room temperature and the supernatant was removed and the pellet was resuspended in 2-3 mL of PBS. The suspension was centrifuged again at 35000 rpm for 7 minutes at room temperature, and once again the supernatant was removed. The pellet was resuspended in a hypotonic buffer on ice for 10 minutes, homogenized, and centrifuged at 3000 rpm for 8 minutes at 4° C. The supernatant was kept as it contained the caspase 3 and a protein estimation was performed on it.

Caspase 3 Activity Assay

A fluorescence assay was used to evaluate the presence of active Caspase 3. DEVD-AFC (MP-Biomedicals, Aurora, Ohio) was used as the fluorescent substrate. The substrate, in the presence of DEVD Buffer (0.1 M Hepes, pH 7.4, 2 mM DTT, 0.1% CHAPS, 1% sucrose) and active caspase 3 was incubated at 37° C. for 60 minutes and fluorescence was measured at 400 nm excitation and 505 nm emission using the spectra max Gemini XS (Molecular Devices, Sunnyvale, Calif.). Caspase 3 activity was measured as relative to the level of fluorescence.

Treatment of Active Caspase 3 with sdAbs and Measurement of Fluorescence

Following the protocol set out above, the effects on activity of Caspase 3 could be monitored upon treatment with the sdAbs. The sdAbs were added so that concentration would be equal to that of the isolated caspase 3 and decreases in fluorescence could be monitored as the decrease in activity of Caspase 3. The sdAbs were Incubated with the active caspase 3 for 30 minutes at 37° C. prior to the addition of the DEVD-AFC buffer and substrate. Following incubation, the caspase and sdAbs were added to DEVD buffer in a 96 well plate and the substrate was added. This was Incubated for 60 minutes and fluorescence was read.

Each experiment was performed in triplicate as described above and this was done four times. The control was active caspase 3+DEVD buffer+DEVD-AFC, with caspase 3 single domain antibody 1 decreasing caspase 3 activity and single domain antibody 2 increasing caspase 3 activity (FIG. 18).

It is understood that the examples described above in no way serve to limit the true scope of this invention, bur rather are presented for illustrative purposes.

REFERENCES

Adhihetty, P. J. and Hood, D. A. (2003). Mechanisms of Apoptosis in Skeletal Muscle. Basic Appl. Myol. 13: 171-179.

Aires da Silva, F., Santa-Marta, M., Freitas-Vieira, A., Mascarenhas, P., Barahona, I., Moniz-Pereira, J., Gabuzda, D., and Goncalves, J. (Jul. 9, 2004). Camelized rabbit-derived VH single-domain intrabodies against Vif strongly neutralize HIV-1 infectivity. J Mol. Biol. 340: 525-542.

Battistutta, R., Negro, A., and Zanotti, G. (Dec. 1, 2000). Crystal structure and refolding properties of the mutant F99S/M153T/V163A of the green fluorescent protein. Proteins 41: 429-437.

Colby, D. W., Garg, P., Holden, T., Chao, G., Webster, J. M., Messer, A., Ingram, V. M., and Wittrup, K. D. (Sep. 17, 2004). Development of a human light chain variable domain (V(L)) intracellular antibody specific for the amino terminus of huntingtin via yeast surface display. J Mol. Biol. 342: 901-912.

Hamers-Casterman C., Atarhouch, T., Muyldermans, S., Robinson, G., Hamers, C., Songa, E. B., Bendahman, N., and Hamers, R. (Jun. 3, 1993). Naturally occurring antibodies devoid of light chains. Nature 363: 446-448.

Kontermann, R. E. (2004). Intrabodies as therapeutic agents. Methods 34: 163-170.

Li, N., Ragheb, K., Lawler, G., Sturgis, J., Rajwa, B., Melendez, J. A., and Robinson, J. P. (Mar. 7, 2003a). Mitochondrial complex I inhibitor rotenone induces apoptosis through enhancing mitochondrial reactive oxygen species production. J Biol. Chem 278: 8516-8525.

Li, N., Ragheb, K., Lawler, G., Sturgis, J., Rajwa, B., Melendez, J. A., and Robinson, J. P. (Mar. 7, 2003b). Mitochondrial complex I inhibitor rotenone induces apoptosis through enhancing mitochondrial reactive oxygen species production. J Biol. Chem 278: 8516-8525.

Miller, T. W. and Messer, A. (Jun. 15, 2005). Intrabody applications in neurological disorders: progress and future prospects. Mol. Ther. 12: 394-401.

Nomura, K., Imai, H., Koumura, T., Kobayashi, T., and Nakagawa, Y. (Oct. 1, 2000). Mitochondrial phospholipid hydroperoxide glutathione peroxidase inhibits the release of cytochrome c from mitochondria by suppressing the peroxidation of cardiolipin in hypoglycaemia-induced apoptosis. Biochem. J 351: 183-193.

Pace, C. N., Vajdos, F., Fee, L., Grimsley, G., and Gray, T. (1995). How to measure and predict the molar absorption coefficient of a protein. Protein Sci. 4: 2411-2423.

Rondon, I. J. and Marasco, W. A. (1997). Intracellular antibodies (Intrabodies) for gene therapy of infectious diseases. Annu. Rev. Microbiol. 51: 257-283.

Sambrook, J. F. E. F. a. M. T. (1989). "Molecular Cloning: A laboratory Manual ($2^{nd}$ ed.)", Cold Spring Harbor Laboratory, Cold Spring Harbor, N.Y.

Somayajulu, M., McCarthy, S., Hung, M., Sikorska, M., Borowy-Borowski, H., and Pandey, S. (2005). Role of mitochondria in neuronal cell death induced by oxidative stress; neuroprotection by Coenzyme Q10. Neurobiol. Dis. 18: 618-627.

Sunderman, F. W., Jr., Marzouk, A., Hopfer, S. M., Zaharia, O., and Reid, M. C. (1985). Increased lipid peroxidation in tissues of nickel chloride-treated rats. Ann. Clin. Lab Sci. 15: 229-236.

Sunderman, F. W. J. N., Marzouk, A., HopferMiki, S. M., Zaharia, O. A., and Reid, M. C. T. (Mar. 10, 1985). Increased lipid peroxidation in tissuestissuesRole of nickel chloride-treated ratsthe mitochondrial permeability transition and cytochrome C release in hydrogen peroxide-induced apoptosis. Ann. Clin. Lab Sci Exp. Cell Res. 15274: 22916-23624.

Susin, S. A., Lorenzo, H. K., Zamzami, N., Marzo, I., Snow, B. E., Brothers, G. M., Mangion, J., Jacotot, E., Costantini, P., Loeffler, M., Larochette, N., Goodlett, D. R., Aebersold, R., Siderovski, D. P., Penninger, J. M., and Kroemer, G. (Feb. 4, 1999). Molecular characterization of mitochondrial apoptosis-inducing factor. Nature 397: 441-446.

Tanaka, T., Lobato, M. N., and Rabbitts, T. H. (Aug. 29, 2003). Single domain intracellular antibodies: a minimal fragment for direct in vivo selection of antigen-specific intrabodies. J Mol. Biol. 331: 1109-1120.

Tanha, J., Dubuc, G., Hirama, T., Narang, S. A., and MacKenzie, C. R. (May 1, 2002a). Selection by phage display of llama conventional V(H) fragments with heavy chain antibody V(H)H properties. J. Immunol. Methods 263: 97-109.

Tanha, J., Dubuc, G., Hirama, T., Narang, S. A., and MacKenzie, C. R. (May 1, 2002b). Selection by phage display of llama conventional V(H) fragments with heavy chain antibody V(H)H properties. J. Immunol. Methods 263: 97-109.

Tanha, J., Dubuc, G., Hirama, T., Narang, S. A., and MacKenzie, C. R. (May 1, 2002c). Selection by phage display of llama conventional V(H) fragments with heavy chain antibody V(H)H properties. J. Immunol. Methods 263: 97-109.

Tanha, J., Dubuc, G., Hirama, T., Narang, S. A., and MacKenzie, C. R. (May 1, 2002d). Selection by phage display of llama conventional V(H) fragments with heavy chain antibody V(H)H properties. J. Immunol. Methods 263: 97-109.

Tanha, J., Dubuc, G., Hirama, T., Narang, S. A., and MacKenzie, C. R. (May 1, 2002e). Selection by phage display of llama conventional V(H) fragments with heavy chain antibody V(H)H properties. J. Immunol. Methods 263: 97-109.

Tanha, J., Muruganandam, A., and Stanimirovic, D. (2003). Phage Display Technology for Identifying Specific Antigens on Brain Endothelial Cells. Methods Mol. Med. 89: 435-450.

Yau, K. Y., Dubuc, G., Li, S., Hirama, T., MacKenzie, C. R., Jermutus, L., Hall, J. C., and Tanha, J. (2005). Affinity maturation of a V(H)H by mutational hotspot randomization. J Immunol Methods 297: 213-224.

REFERENCES

Adhihetty, P. J. and Hood, D. A. (2003). Mechanisms of Apoptosis In Skeletal Muscle. Basic Appl. Myol. 13: 171-179.

Aires da Silva, F., Santa-Marta, M., Freitas-Vieira, A., Mascarenhas, P., Barahona, I., Moniz-Pereira, J., Gabuzda, D., and Goncalves, J. (Jul. 9, 2004). Camelized rabbit-derived VH single-domain Intrabodies against Vif strongly neutralize HIV-1 infectivity. J Mol. Biol. 340: 525-542.

Battistutta, R., Negro, A., and Zanotti, G. (Dec. 1, 2000). Crystal structure and refolding properties of the mutant F99S/M153T/V163A of the green fluorescent protein. Proteins 41: 429-437.

Colby, D. W., Garg, P., Holden, T., Chao, G., Webster, J. M., Messer, A., Ingram, V. M., and Wittrup, K. D. (Sep. 17, 2004). Development of a human light chain variable domain (V(L)) intracellular antibody specific for the amino terminus of huntingtin via yeast surface display. J Mol. Biol. 342: 901-912.

Hamers-Casterman C., Atarhouch, T., Muyldermans, S., Robinson, G., Hamers, C., Songa, E. B., Bendahman, N., and Hamers, R. (Jun. 3, 1993). Naturally occurring antibodies devoid of light chains. Nature 363: 446-448.

Kontermann, R. E. (2004). Intrabodies as therapeutic agents. Methods 34: 163-170.

Li, N., Ragheb, K., Lawler, G., Sturgis, J., Rajwa, B., Melendez, J. A., and Robinson, J. P. (Mar. 7, 2003a). Mitochondrial complex I inhibitor rotenone induces apoptosis through enhancing mitochondrial reactive oxygen species production. J Biol. Chem 278: 8516-8525.

Li, N., Ragheb, K., Lawler, G., Sturgis, J., Rajwa, B., Melendez, J. A., and Robinson, J. P. (Mar. 7, 2003b). Mitochondrial complex I inhibitor rotenone induces apoptosis through enhancing mitochondrial reactive oxygen species production. J Biol. Chem 278: 8516-8525.

Miller, T. W. and Messer, A. (Jun. 15, 2005). Intrabody applications in neurological disorders: progress and future prospects. Mol. Ther. 12: 394-401.

Nomura, K., Imai, H., Koumura, T., Kobayashi, T., and Nakagawa, Y. (Oct. 1, 2000). Mitochondrial phospholipid hydroperoxide glutathione peroxidase inhibits the release of cytochrome c from mitochondria by suppressing the peroxidation of cardiolipin in hypoglycaemia-induced apoptosis. Biochem. J 351: 183-193.

Pace, C. N., Vajdos, F., Fee, L., Grimsley, G., and Gray, T. (1995). How to measure and predict the molar absorption coefficient of a protein. Protein Sci. 4: 2411-2423.

Rondon, I. J. and Marasco, W. A. (1997). Intracellular antibodies (intrabodies) for gene therapy of infectious diseases. Annu. Rev. Microbiol. 51: 257-283.

Sambrook, J. F. E. F. a. M. T. (1989). "Molecular Cloning: A laboratory Manual (2$^{nd}$ ed.)", Cold Spring Harbor Laboratory, Cold Spring Harbor, N.Y.

Somayajulu, M., McCarthy, S., Hung, M., Sikorska, M., Borowy-Borowski, H., and Pandey, S. (2005). Role of mitochondria in neuronal cell death induced by oxidative stress; neuroprotection by Coenzyme Q10. Neurobiol. Dis. 18: 618-627.

Sunderman, F. W., Jr., Marzouk, A., Hopfer, S. M., Zaharia, O., and Reid, M. C. (1985). Increased lipid peroxidation in tissues of nickel chloride-treated rats. Ann. Clin. Lab Sci. 15: 229-236.

Sunderman, F. W. J. N., Marzouk, A., HopferMiki, S. M., Zaharia, O. A., and Reid, M. C. T. (Mar. 10, 1985). Increased lipid peroxidation in tissuestissuesRole of nickel chloride-treated ratsthe mitochondrial permeability transition and cytochrome C release in hydrogen peroxide-induced apoptosis. Ann. Clin. Lab Sci Exp. Cell Res. 15274: 22916-23624.

Susin, S. A., Lorenzo, H. K., Zamzami, N., Marzo, I., Snow, B. E., Brothers, G. M., Mangion, J., Jacotot, E., Costantini, P., Loeffler, M., Larochette, N., Goodlett, D. R., Aebersold, R., Siderovski, D. P., Penninger, J. M., and Kroemer, G. (24-1999). Molecular characterization of mitochondrial apoptosis-inducing factor. Nature 397: 441-446.

Tanaka, T., Lobato, M. N., and Rabbitts, T. H. (Aug. 29, 2003). Single domain intracellular antibodies: a minimal fragment for direct in vivo selection of antigen-specific intrabodies. J Mol. Biol. 331: 1109-1120.

Tanha, J., Dubuc, G., Hirama, T., Narang, S. A., and MacKenzie, C. R. (May 1, 2002a). Selection by phage display of llama conventional V(H) fragments with heavy chain antibody V(H)H properties. J. Immunol. Methods 263: 97-109.

Tanha, J., Dubuc, G., Hirama, T., Narang, S. A., and MacKenzie, C. R. (May 1, 2002b). Selection by phage display of llama conventional V(H) fragments with heavy chain antibody V(H)H properties. J. Immunol. Methods 263: 97-109.

Tanha, J., Dubuc, G., Hirama, T., Narang, S. A., and MacKenzie, C. R. (May 1, 2002c). Selection by phage display of llama conventional V(H) fragments with heavy chain antibody V(H)H properties. J. Immunol. Methods 263: 97-109.

Tanha, J., Dubuc, G., Hirama, T., Narang, S. A., and MacKenzie, C. R. (May 1, 2002d). Selection by phage display of llama conventional V(H) fragments with heavy chain antibody V(H)H properties. J. Immunol. Methods 263: 97-109.

Tanha, J., Dubuc, G., Hirama, T., Narang, S. A., and MacKenzie, C. R. (May 1, 2002e). Selection by phage display of llama conventional V(H) fragments with heavy chain antibody V(H)H properties. J. Immunol. Methods 263: 97-109.

Tanha, J., Muruganandam, A., and Stanimirovic, D. (2003). Phage Display Technology for Identifying Specific Antigens on Brain Endothelial Cells. Methods Mol. Med. 89: 435-450.

Yau, K. Y., Dubuc, G., Li, S., Hirama, T., MacKenzie, C. R., Jermutus, L., Hall, J. C., and Tanha, J. (2005). Affinity maturation of a V(H)H by mutational hotspot randomization. J Immunol Methods 297: 213-224.

Yau, K. Y., Groves, M. A., Li, S., Sheedy, C., Lee, H., Tanha, J., MacKenzie, C. R., Jermutus, L., and Hall, J. C. (2003). Selection of hapten-specific single-domain antibodies from a non-immunized llama ribosome display library. J. Immunol. Methods 281: 161-175.

Zhang, J., Tanha, J., Hirama, T., Khieu, N. H., To, R., Tong-Sevinc, H., Stone, E., Brisson, J. R., and MacKenzie, C. R. (Jan. 2, 2004a). Pentamerization of Single-domain Antibodies from Phage Libraries: A Novel Strategy for the Rapid Generation of High-avidity Antibody Reagents. J. Mol. Biol. 335: 49-56.

Zhang, J., Tanha, J., Hirama, T., Khieu, N. H., To, R., Tong-Sevinc, H., Stone, E., Brisson, J. R., and MacKenzie, C. R. (Jan. 2, 2004b). Pentamerization of Single-domain Antibodies from Phage Libraries: A Novel Strategy for the Rapid Generation of High-avidity Antibody Reagents. J. Mol. Biol. 335: 49-56.

Zhang, J., Tanha, J., Hirama, T., Khieu, N. H., To, R., Tong-Sevinc, H., Stone, E., Brisson, J. R., and MacKenzie, C. R. (Jan. 2, 2004c). Pentamerization of Single-domain Antibodies from Phage Libraries: A Novel Strategy for the Rapid Generation of High-avidity Antibody Reagents. J. Mol. Biol. 335: 49-56.

Zhang, J., Tanha, J., Hirama, T., Khieu, N. H., To, R., Tong-Sevinc, H., Stone, E., Brisson, J. R., and MacKenzie, C. R. (Jan. 2, 2004d). Pentamerization of Single-domain Antibodies from Phage Libraries: A Novel Strategy for the Rapid Generation of High-avidity Antibody Reagents. J. Mol. Biol. 335: 49-56.

Kabat, E. A., Wu, T. T., Perry, H. M., Gottesman, K. S. & Foeller, C. Sequences of proteins of immunological interest. US Department of Health and Human Services, US Public Health Service, Bethesda, Md. (1991).

We claim:

1. An isolated single-domain antibody having an amino acid sequence that comprises at least one of SEQ. ID. NO.: 1, SEQ ID NO.:2, SEQ ID NO.: 3, SEQ ID NO.: 4, SEQ ID NO. 5, and SEQ ID NO.: 6.

2. A single-domain antibody as claimed in claim 1 that is fused to a polypeptide.

3. A single-domain antibody as claimed in claim 1 that is fused to an antibody domain.

4. A single-domain antibody as claimed in claim 3 wherein the antibody domain is a Immunoglobulin (Ig) light chain variable domain ($V_L$), an Ig heavy chain variable domain ($V_H$), a camelid (camels and llamas) heavy chain antibody variable domain ($V_HH$), a nurse shark and wobbegong shark Ig new antigen receptor (IgNAR) variable domain ($V_H$), or a T cell receptor variable domain.

5. A single-domain antibody as claimed in claim 2 wherein the polypeptide is a marker protein.

6. A single-domain antibody as claimed in claim 2 wherein the polypeptide is a signal protein or sequence determining cellular localization.

7. A single-domain antibody as claimed in claim 6 wherein the signal protein is a mitochondrial transport signal protein.

8. A single-domain antibody as claimed in claim 2 wherein the polypeptide has the ability to cross cell membranes.

9. A single-domain antibody as claimed in claim 8 wherein the polypeptide is a membrane translocating sequence or protein transduction domain.

10. A single-domain antibody as claimed in claim 8 wherein the polypeptide is an internalizing protein.

11. An immunoliposome comprising a single-domain antibody as claimed in claim 1.

12. A multimer comprising at least two single-domain antibodies as claimed in claim 1.

13. A multimer as claimed in claim 12 comprising five single-domain antibodies.

14. An isolated single-domain antibody having a binding affinity for Bax and having an amino acid sequence encoded by a nucleic acid sequence that comprises at least one of SEQ ID NO.: 10, SEQ ID NO.: 11, SEQ ID NO.: 12, SEQ ID NO.: 13, SEQ ID NO.:14, and SEQ ID NO.: 15.

15. A method for modulating the effects of oxidative stress in a cell, in vitro or ex vivo, the method comprising the steps of exposing the cell to at least one single-domain antibody that comprises at least one of SEQ ID NO.: 1, SEQ ID NO.: 2, SEQ ID NO.: 3, SEQ ID NO.: 4, SEQ ID NO.: 5, and/or SEQ ID NO.: 6 and allowing binding of the at least one single-domain antibody to Bax.

16. A method as claimed in claim 15 further comprising the steps of delivering a nucleic acid sequence which encodes the at least one single-domain antibody or antibody fragment into the cell; and allowing expression of the at least one single-domain antibody or antibody fragment in the cell.

17. A method as claimed in claim 15 further comprising the steps of fusing the single-domain antibody or antibody fragment to a polypeptide which permits membrane translocation or internalization of the single-domain antibody or antibody fragment into the cell.

18. A method for identifying a second single-domain antibody having a binding affinity for an apoptotic protein, comprising the steps of:
   a) providing a first single-domain antibody as defined in claim 1;
   b) constructing an antibody library based on a structure of the first single-domain antibody; and
   c) screening the antibody library for single-domain antibodies having a binding affinity for the apoptotic protein.

* * * * *